(12) United States Patent
Brody et al.

(10) Patent No.: US 10,570,454 B2
(45) Date of Patent: Feb. 25, 2020

(54) METHODS OF IDENTIFYING INDIVIDUALS AT INCREASED RISK OF LUNG CANCER

(71) Applicants: Trustees of Boston University, Boston, MA (US); University of Utah Research Foundation, Salt Lake City, UT (US)

(72) Inventors: Jerome S. Brody, Boston, MA (US); Avrum Spira, Newton, MA (US); Adam Gustafson, Portland, OR (US); Andrea Bild, Salt Lake City, UT (US)

(73) Assignees: Trustees of Boston University, Boston, MA (US); University of Utah Research Foundation, Salt Lake City, UT (US)

( * ) Notice: Subject to any disclaimer, the term of this patent is extended or adjusted under 35 U.S.C. 154(b) by 141 days.

(21) Appl. No.: 14/500,475

(22) Filed: Sep. 29, 2014

(65) Prior Publication Data

US 2015/0232945 A1    Aug. 20, 2015

Related U.S. Application Data

(63) Continuation of application No. 12/234,588, filed on Sep. 19, 2008, now abandoned.

(60) Provisional application No. 60/994,643, filed on Sep. 19, 2007.

(51) Int. Cl.

| *C12Q 1/6886* | (2018.01) |
| *A61K 31/047* | (2006.01) |
| *A61K 31/5377* | (2006.01) |
| *C12Q 1/48* | (2006.01) |
| *C12Q 1/6809* | (2018.01) |

(52) U.S. Cl.
CPC .......... *C12Q 1/6886* (2013.01); *A61K 31/047* (2013.01); *A61K 31/5377* (2013.01); *C12Q 1/485* (2013.01); *C12Q 1/6809* (2013.01); *C12Q 2600/158* (2013.01); *C12Q 2600/16* (2013.01); *G01N 2333/91205* (2013.01); *G01N 2800/50* (2013.01); *G01N 2800/7028* (2013.01)

(58) Field of Classification Search
None
See application file for complete search history.

(56) References Cited

U.S. PATENT DOCUMENTS

| 3,640,268 A | 2/1972 | Davis |
| 4,641,662 A | 2/1987 | Jaicks |
| 4,800,896 A | 1/1989 | Jalowayski |
| 5,422,273 A | 6/1995 | Garrison |
| 5,440,942 A | 8/1995 | Hubbard |
| 5,477,863 A | 12/1995 | Grant |
| 5,726,060 A | 3/1998 | Bridges |
| 5,795,782 A | 8/1998 | Church et al. |
| 5,876,978 A | 3/1999 | Willey et al. |
| 6,085,907 A | 7/2000 | Hochmeister |
| 6,746,846 B1 | 6/2004 | Wang et al. |
| 2002/0081612 A1 | 6/2002 | Katz et al. |
| 2002/0094547 A1 | 7/2002 | Burstein |
| 2002/0160388 A1 | 10/2002 | Macina et al. |
| 2003/0104499 A1 | 6/2003 | Pressman et al. |
| 2004/0005294 A1 | 1/2004 | Lee |
| 2004/0009489 A1 | 1/2004 | Golub et al. |
| 2004/0063120 A1 | 4/2004 | Beer et al. |
| 2004/0197785 A1 | 10/2004 | Willey et al. |
| 2004/0241725 A1 | 12/2004 | Xiao et al. |
| 2004/0241728 A1 | 12/2004 | Liew |
| 2005/0260586 A1 | 11/2005 | Demuth et al. |
| 2005/0266409 A1 | 12/2005 | Brown et al. |
| 2006/0127928 A1 | 6/2006 | Bacus et al. |
| 2006/0140960 A1* | 6/2006 | Wang ............... A61K 31/00 424/155.1 |
| 2006/0154278 A1 | 7/2006 | Brody et al. |
| 2006/0183144 A1 | 8/2006 | Willey et al. |
| 2006/0188909 A1 | 8/2006 | Willey et al. |
| 2006/0190192 A1 | 8/2006 | Willey et al. |
| 2006/0194216 A1 | 8/2006 | Willey et al. |
| 2007/0092891 A1 | 4/2007 | Willey et al. |
| 2007/0092892 A1 | 4/2007 | Willey et al. |
| 2007/0092893 A1 | 4/2007 | Willey et al. |
| 2007/0148650 A1 | 6/2007 | Brody et al. |
| 2009/0061454 A1 | 3/2009 | Brody et al. |

(Continued)

FOREIGN PATENT DOCUMENTS

| CN | 1688582 A | 10/2005 |
| DE | 10219117 | 10/2003 |

(Continued)

OTHER PUBLICATIONS

Tsao et al. (Cancer Epidemiology, Biomarkers & Prevention, vol. 12, 660-664, Jul. 2003).*
Liao et al. (Abstract only, Ai Zheng 25:10, p. 1238-42 (2006)).*
Tichelaar et al. (BMC Cancer 2005, 5:155, thirteen pages).*
Saal et al. (PNAS May 2007, vol. 104, No. 18, pp. 7564-7569).*
West et al. (The Journal of Clinical Investigation, Jan. 2003, vol. 11, No. 1, pp. 81-90).*
Slonin, Nature Genetics Supplement, vol. 32, Dec. 2002, pp. 502-508.*
Baker. Journal of the National Cancer Institute, vol. 95, No. 7, Apr. 2, 2003, pp. 511-515.*

(Continued)

*Primary Examiner* — Alana Harris Dent
(74) *Attorney, Agent, or Firm* — Morse, Barnes-Brown & Pendleton, P.C.; Lisa M. Warren, Esq.

(57) ABSTRACT

The invention provides the identification of oncogenic pathways activated in cytologically normal airway cells of individuals having or at risk of having lung disease, as well as specific gene expression patterns (biomarkers) associated with pathway activation. These biomarkers and pathways may provide prognostic and/or diagnostic indicators in lung disease, e.g., lung cancer. Additionally, these pathways and biomarkers may provide therapeutic targets for the treatment of lung disease, as well as markers for the assessment of treatment efficacy.

3 Claims, 5 Drawing Sheets

(56) References Cited

U.S. PATENT DOCUMENTS

| | | |
|---|---|---|
| 2009/0186951 A1 | 7/2009 | Brody et al. |
| 2009/0246779 A1 | 10/2009 | Rabinovitch et al. |
| 2009/0311692 A1 | 12/2009 | Brody et al. |
| 2010/0035244 A1 | 2/2010 | Brody et al. |
| 2010/0055689 A1 | 3/2010 | Spira et al. |
| 2011/0053158 A1 | 3/2011 | Mambo et al. |
| 2011/0190150 A1 | 8/2011 | Brody et al. |
| 2011/0217717 A1 | 9/2011 | Brody et al. |
| 2012/0041686 A1 | 2/2012 | Brody et al. |
| 2012/0190567 A1 | 7/2012 | Brody et al. |
| 2012/0288860 A1 | 11/2012 | Van et al. |
| 2012/0322673 A1 | 12/2012 | Brody et al. |
| 2013/0023437 A1 | 1/2013 | Brody et al. |
| 2013/0303826 A1 | 11/2013 | Jurisica et al. |
| 2014/0378425 A1 | 12/2014 | Wilde et al. |
| 2015/0080243 A1 | 3/2015 | Whitney et al. |
| 2015/0088430 A1 | 3/2015 | Whitney et al. |
| 2015/0152474 A1 | 6/2015 | Pawlowski et al. |
| 2015/0354008 A1 | 12/2015 | Brody et al. |
| 2016/0024583 A1 | 1/2016 | Whitney et al. |
| 2016/0130656 A1 | 5/2016 | Whitney et al. |
| 2017/0226591 A1 | 8/2017 | Brody et al. |
| 2017/0247759 A1 | 8/2017 | Wilde et al. |
| 2017/0328908 A1 | 11/2017 | Brody et al. |
| 2018/0171418 A1 | 6/2018 | Brody et al. |

FOREIGN PATENT DOCUMENTS

| | | |
|---|---|---|
| WO | WO/1999/060160 A1 | 11/1999 |
| WO | WO 2000/006780 | 2/2000 |
| WO | WO 2001/028428 | 4/2001 |
| WO | WO 2002/006791 | 1/2002 |
| WO | WO 02/44331 | 6/2002 |
| WO | WO 2002/072866 | 9/2002 |
| WO | WO/2002/086443 A2 | 10/2002 |
| WO | WO 2003/015613 | 2/2003 |
| WO | WO/2003/040325 A2 | 5/2003 |
| WO | WO/2004/005891 A2 | 1/2004 |
| WO | WO 2004/029055 | 4/2004 |
| WO | WO/2004/091511 A2 | 10/2004 |
| WO | WO/2004/111197 A2 | 12/2004 |
| WO | WO/2005/000098 A2 | 1/2005 |
| WO | WO/2005/047451 A2 | 5/2005 |
| WO | WO 2006/056080 | 6/2006 |
| WO | WO/2006/113467 A3 | 10/2006 |
| WO | WO/2007/103541 A2 | 9/2007 |
| WO | WO/2009/039457 A2 | 3/2009 |
| WO | WO/2009/029273 A2 | 4/2009 |
| WO | WO2009/121070 A1 | 10/2009 |
| WO | WO 2010/054233 | 5/2010 |
| WO | WO 2013/033640 | 3/2013 |
| WO | WO 2013/049152 | 4/2013 |
| WO | WO 2013/163568 | 10/2013 |
| WO | WO 2013/177060 A2 | 11/2013 |
| WO | WO 2014/144564 | 9/2014 |
| WO | WO 2014/186036 | 11/2014 |
| WO | WO 2016/011068 | 1/2016 |
| WO | WO 2017/197335 | 11/2017 |
| WO | WO 2018/009915 | 1/2018 |
| WO | WO 2018/048960 | 3/2018 |

OTHER PUBLICATIONS

Watters et al. (Mol Cancer Ther 2006; 5(10) Oct. 2006, pp. 2444-2449.*
Thisted. http://www.stat.uchicago.edu/~thisted. six pages. 1998.*
Sotos et al. Statistics Education Research Journal, 8(2), 33-55, http://www.stat.auckland.ac.nz/serj.*
Langford et al. The American Statistician, Nov. 2001, vol. 55, No. 4, pp. 322-332.*
Schulz et al. Chest 125(5):1706-1713, May 2004.*
St. Croix, et al., "Genes Expressed in Human Tumor Endothelium," Science, 289:1197-1202, (Aug. 18, 2000).
Final Office Action from U.S. Appl. No. 11/294,834, dated Aug. 22, 2016.
Details for HG-U133A:217291 _AT (CEACAM5) (https://www.affymetrix.com/analysis/netaffx/fullrecord.affx?pk=HG-U133A:217291 _AT, downloaded Apr. 22, 2016).
Mollerup, et al., "Sex Differences in Lung CYP1A1 Expression and DNA Adduct Levels among Lung Cancer Patients," Cancer Research, 1999, 59: 3317-3320 (1999).
Saito-Hisaminato, "Genome-Wide Profiling of Gene Expression in 29 Normal Human Tissues with a cNDA Microarray," DNA Research, 2002, 9:35-45.
Willey, et al., "Quantitative RT-PCR Measurement of Cytochromes p450 1A1, 1B1, and 2B7, Microsomal Epoxide Hydrolase, and NADPH Oxidoreductase Expression in Lung Cells of Smokers and Nonsmokers," Am. J. Respir. Cell Mol. Biol., 1997, 17:114-124.
Non-Final Office Action for U.S. Appl. No. 14/584,960, dated Apr. 27, 2016.
Möller, et al., "Altered Ratio of Endothelin $ET_A$- and $ET_B$ Receptor mRNA in Bronchial Biopsies from Patients with Asthma and Chronic Airway Obstruction," European Journal of Pharmacology, 365:R1-R3, (1999).
Wojnarowski, et al., "Cytokine Expression in Bronchial Biopsies of Cystic Fibrosis Patients With and Without Acute Exacerbation," Eur. Respir. J., 14:1136-1144, (1999).
Non-Final Office Action from U.S. Appl. No. 14/613,210, dated Dec. 6, 2016.
Brambilla, et al., "Advances in Brief p53 Mutant Immunophenotype and Deregulation of p53 Transcription Pathway (Bcl2, Bax, and Waft) in Precursor Bronchial Lesions of Lung Cancer1", Clinical Cancer Research, 4: 1609-1618 (1998).
Demuth, et al., "The gene expression index c-myc x E2F-1/p21 is highly predictive of malignant phenotype in human bronchial epithelial cells", American Journal of Respiratory Cell and Molecular Biology, 19: 18-24 (1998).
Hirsch, et al., "Early Detection of Lung Cancer: Clinical Perspectives of Recent Advances in Biology and Radiology 1", Clinical Cancer Research, 7: 5-22 (2001).
Lacroix, et al., "Sensitive detection of rare cancer cells in sputum and peripheral blood samples of patients with lung cancer by preproGRP-specific RT-PCR", International Journal of Cancer, 92(1): 1-8 (2001).
Abrahamson, et al., Cystatins. Biochem. Soc. Symp. 70: 179-199 (2003).
Anderson, et al., National Vital Statistics Report; 52(9): 1-88 (Nov. 7, 2003).
Anthonisen, et al., Effects of Smoking Intervention and the Use of an Inhaled Anticholinergic Bronchodilator on the Rate of Decline of FEV1. JAMA; 272(19):1497-1505 (Nov. 16, 1994).
Beane, et al., A Prediction Model for Lung Cancer Diagnosis that Integrates Genomic and Clinical Features, Cancer Prev Res 2008, 1:56-64 (2008).
Beane, et al., Reversible and permanent effects of tobacco smoke exposure on airway epithelial gene expression. Genome Biology 2007, 8:R201 (Sep. 25, 2007).
Beer, et al., Gene-expression profiles predict survival of patients with lung adenocarcinoma. Nature Medicine, 8: 816-824 (2002).
Belinksky, et al., Aberrant promoter methylation in bronchial epithelium and sputum from current and former smokers. Cancer Res., 62(8): 2370-7 (2002).
Berman, Jeffrey S, Abstract Immunopathology of the nasal mucosa in sarcoidosis National Institutes of Health Grant No. 1 R21 HL077498-01 (Funding Start Date Sep. 15, 2004).
Beum, et al., Epidermal Growth Factor Downregulates Core 2 Enzymes in a Human Airway Adenocarcinoma Cell Line. Am. J. Respir. Cell Mol. Biol., 29:48-56 (2003).
Bhattacharjee, et al., Classification of human lung carcinoma by mRNA expression profiling reveals distinct adenocarcinoma subclasses. Proc Natl Acad Sci USA, 98(24): 13790-5 (Nov. 20, 2001).
Bild, et al., Oncogenic pathway signatures in human cancers as a guide to targeted therapies. Nature, 439: 353-357 (2006).
Chari, et al., Effect of active smoking on the human bronchial epithelium transcriptome. BMC Genomics, 8:297 (Aug. 29, 2007).

(56) References Cited

OTHER PUBLICATIONS

Clark, A., et al., "Altered Protein Kinase C (PKC) Isoforms in Non-Small Cell Lung Cancer Cells: PKCdelta Promotes Cellular Survival and Chemotherapeutic Resistance," *Cancer Research*, 63(4): 780-786 (2003).
Crawford, et al., Normal Bronchial Epithelial Cell Expression of Glutathione Transferase P1, Glutathione Transferase M3, and Glutathione Peroxidase is Low in Subjects with Bronchogenic Carcinoma. Cancer Research. 60: 1609-1618 (Mar. 15, 2000).
Cummings, SR. et al., Estimating the probability of malignancy in solitary pulmonary nodules. A Bayesian approach, Am Rev Respir Dis 1986;134:449-52 (1986).
Demeo, et al., The SERPINE2 gene is associated with chronic obstructive pulmonary disease. Am J Hum Genet., 78(2): 253-264 (Feb. 2006).
Denis, et al., RING3 Kinase Transactivates Promoters of Cell Cycle Regulatory Genes through E2F1 Cell. Growth Differ; 11: 417-424 (Aug. 2000).
Doll, R. et al., Mortality in relation to smoking: 40 years' observations on male British doctors. BMJ; 309:901-911 (Oct. 8, 1994).
Ebbert, et al., Lung Cancer Risk Reduction After Smoking Cessation: Observations From a Prospective Cohort of Women. J Clin Oncol; 21(5):921-926 (Mar. 1, 2003).
Fahy, JV. Remodeling of the Airway Epithelium in Asthma. Am. J. Respir. Crit. Care Med. 164:S46-S51 (2001).
Freeman, et al., DNA from Buccal Swabs Recruited by Mail: Evaluation of Storage Effects on Long-term Stability and Suitability for Multiplex Polymerase Chain Reaction Genotyping, *Behavior Genetics*, 33: 67 (2003).
Garber, et al., Diversity of gene expression in adenocarcinoma of the lung. PNAS, 98(24): 13784-13789 (Nov. 20, 2001).
Garcia-Closas, Collection of Genomic DNA from Adults in Epidemiological Studies by Buccal Cytobrush and Mouthwash, Cancer Epidemiology, Biomarkers and Prevention, 10: 687-696, (2001).
Gebel, et al., Gene expression profiling in respiratory tissues from rats exposed to mainstream cigarette smoke. Carcinogenesis, 25(2): 169-178 (2004).
Golub, et al., Molecular classification of cancer: Class discovery and class prediction by gene expression monitoring, Science, American Association for the Advancement of Science, 286:5439 (Oct. 15, 1999).
Greenlee, et al., Cancer Statistics, 2001. CA Cancer J Clin; 51(1):15-36 (2001).
Gurney, JW. Determining the likelihood of malignancy in solitary pulmonary nodules with Bayesian analysis, Part 1, Theory. Radiology 1993;186:405-13 (2005).
Hackett, et al., Variability of antioxidant-related gene expression in the airway epithelium of cigarette smokers. Am J Respir Cell Mol Biol., 29: 331-43 (2003).
Hecht, SS., Tobacco carcinogens, their biomarkers and tobacco-induced cancer. Nature Review Cancer; 3:733-744 (Oct. 2003).
Jang, et al., Activation of melanoma antigen tumor antigens occurs early in lung carcinogenesis. Cancer Research 61: 7959-7963 (2001).
Kanner, et al., Effects of randomized assignment to a smoking cessation intervention and changes in smoking habits on respiratory symptoms in smokers with early chronic obstructive pulmonary disease: the lung health study. American Journal of Medicine; 106:410-416 (1999).
Kao, et al., Tumor-associated Antigen L6 and the Invasion of Human Lung Cancer Cells. Clin Cancer Res. 9:2807-2816 (Jul. 2003).
Katz, et al., Automated detection of genetic abnormalities combined with cytology in sputum is a sensitive predictor of lung cancer, Modern Pathology;21:950-960 (2008).
Kazemi-Noureini, et al., Differential gene expression between squamous cell carcinoma of esophageus and its normal epithelium; altered pattern of mal, akr1c2, and rab11a expression. World J Gastroenterol, 10(12): 1716-1721 (2004).
Kitahara, et al. Alternations of Gene Expression during Colorectal Carcinogenesis Revealed by cDNA Microarrays after Laser-Capture Microdissection of Tumor Tissues and Normal Epithelia. Cancer Research, 61: 3544-3549 (May 1, 2001).
Lander, et al., Initial sequencing and analysis of the human genome. Nature, 409: 860-921 (Feb. 15, 2001).
Li, L., Survival prediction of diffuse large-B-cell lymphoma based on both clinical and gene expression information, Bioinformatics 2006; 22:466-71 (2006).
Liao, et al., Expression and significance of PTEN/PI3K signal transduction-related proteins in nonsmall cell lung cancer, Ai Zheng 25: 10, p. 1238-42. Abstract (2006).
Liu et al., Effects of physiological versus pharmacological β-carotene supplementation on cell proliferation and histopathological changes in the lungs of cigarette smoke-exposed ferrets. Carcinogenesis, 21: 2245-2253 (2000).
Mannino, DM. et al., Low lung function and incident lung cancer in the United States: data From the First National Health and Nutrition Examination Survey follow-up, Arch Intern Med. 163(12):1475-80 (2003).
Medical News: Targeted, Oral Agent Enzastaurin Shows Favorable Results in Late-Stage Lung Cancer. (Jun. 11, 2007), Retrieved from the Internet <URL: http://www.medicalnewstoday.com/articles/73761.php>.
Michalczyk, et al., Fresh and cultured buccal cells as a source of mRNA and protein for molecular analysis. Biotechniques. 37(2):262-4, 266-9 (2004).
Miklos, et al., Microarray reality checks in the context of a complex disease. Nature Biotechnology, 22:5 (May 2005).
Miura, et al., Laser capture microdissection and microarray expression analysis of lung adenocarcinoma reveals tobacco smoking- and prognosis-related molecular profiles. Cancer Res., 62(11): 3244-50 (Jun. 1, 2002).
Mongiat, et al., Fibroblast Growth Factor-binding Protein Is a Novel Partner for Perlecan Protein Core. The Journal of Biological Chemistry; 276(13):10263-10271 (Mar. 30, 2001).
Neubauer, et al., Cure of Helicobacter pylori Infection and Duration of Remission of Low-Grade Gastric Mucosa-Associated Lymphoid Tissue Lymphoma, J. Natl. Cancer Inst., 89(18): 1350-1378 (Sep. 17, 1997).
Okudela, K., et al., "K-ras Gene Mutation Enhances Motility of Immortalized Airway Cells and Lung Adenocarcinoma Cells via Akt Activation: Possible Contribution to Non-Invasive Expansion of Lung Adenocarcinoma," *The American Journal of Pathology*, 164(1): 91-100 (2004).
Pittman, J. et al., Integrated modeling of clinical and gene expression information fo personalized prediction of disease outcomes, Proc Natl Acad Sci U S A 2004; 101:8431-8436 (2004).
Potti et al., A Genomic Strategy to Refine Prognosis in Early-Stage Non Small-Cell Lung Cancer, The New England Journal of Medicine 2006; 335(6):570-580 (2006).
Powell, et al., Patterns of allelic loss differ in lung adenocarcinomas of smokers and nonsmokers. Lung Cancer, 39(1): 23-29 (2003).
Powell, et al., Gene expression in lung adenocarcinomas of smokers and nonsmokers. American Journal of Respiratory Cell and Molecular Biology, 29: 157-162 (Aug. 2003).
Proctor RN., Tobacco and the global lung cancer epidemic. Nature Reviews Cancer, 1: 82-86 (Oct. 2001).
Rusznak, et al., Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530-536 (2000).
Saheki, et al., Pathogenesis and pathophysiology of citrin (a mitochondrial aspartate glutamate carrier) deficiency. Metabolic Brain Disease; 17(4):335-346 (Dec. 2002).
Schembri, Frank et al., MicroRNAs as modulators of smoking-induced gene expression changes in human airway epithelium, Proc Natl Acad Sci U S A, 106(7):2319-24 (Feb. 2009).
Shields, PG., Molecular epidemiology of lung cancer. Annals of Oncology, 10(5):S7-S11 (1999).
Shriver, et al., Sex-Specific Expression of Gastrin-Releasing Peptide Receptor: Relationship to Smoking History and Risk of Lung Cancer. J. Natl. Cancer Inst., 92: 24-33 (2000).

(56) References Cited

OTHER PUBLICATIONS

Spira, et al., Noninvasive method for obtaining RNA from buccal mucosa epithelial cells for gene expression profiling. Biotechniques, 36(3): 484-7 (2004).
Spira, et al., Effects of cigarette smoke on the human airway epithelial cell transcriptome, PNAS, 101: 27, p. 10143-10148 (Jul. 6, 2004).
Spira, et al., Airway epithelial gene expression in the diagnostic evaluation of smokers with suspect lung cancer. Nature Medicine 13: 361-366 (2007).
Spira, et al., Gene Expression Profiling of Human Lung Tissue from Smokers with Severe Emphysema. Am J Respir Cell Mol Biol., 31(6):601-10 (2004).
Spira, et al., Impact of cigarette smoke on the normal airway transcriptome. Chest. 125 (5 Suppl):115S (May 2004).
Spira, Avrum E., Abstract the airway transcriptome as a biomarker for lung cancer National Institutes of Health Grant No. 1 R21 CA106506-01 (Funding Start Date Aug. 9, 2005).
Spira, Avrum E., Abstract Airway gene expression in smokers: an early diagnostic biomarker for lung cancer National Institutes of Health Grant No. 1 RO1 CA124640-01 (Funding Start Date May 1, 2007).
Spivack, et al., Gene-environment interaction signatures by quantitative mRNA profiling in exfoliated buccal mucosal cells, Cancer Research, 64: 18, p. 6805-6813 (2004).
Sridhar, et al. Smoking-induced gene expression changes in the bronchial airway are reflected in nasal and buccal epithelium. BMC Genomics, 9: 259 (May 2008).
Stephenson, AJ. et al.,Integration of gene expression profiling and clinical variables to predict prostate carcinoma recurrence after radical prostatectomy, Cancer 2005; 104:290-8 (2005).
Stewart, JH. Lung Carcinoma in African Americans, A Review of the Current Literature. Cancer; 91(12): 2476-2482 (Jun. 15, 2001).
Swensen, SJ. et al., The probability of malignancy in solitary pulmonary nodules. Application to small radiologically indeterminate nodules, Arch Intern Med 1997; 157:849-55 (1997).
Swensen, SJ. et al., Abstract Solitary pulmonary nodules: clinical prediction model versus physicians, Mayo Clinic Proc 1999; 74:319-29 (1999).
Theocharis, et al., Metallothionein: a multifunctional protein from toxicity to cancer. Int Biol Markers, 18(3):162-169 (2003).
Thurston, SW. et al., Modeling lung cancer risk in case-control studies using a new dose metric of smoking, Cancer Epidemiol Biomarkers Prey 2005; 14(10): 2296-302 (2005).
Trunk, G. et al., The management and evaluation of the solitary pulmonary nodule, Chest 1974; 66:236-9 (1974).
Ung, YC. et al., Fluorodeoxyglucose positron emission tomography in the diagnosis and staging of lung cancer: a systematic review, J Nat'l Cancer Institute, 99(23): 1753-67 (2007).
Volm, et al., Prognostic significance of the expression of c-fos, c-jun and c-erbB-1 oncogene products in human squamous cell lung carcinomas. J Cancer Res Clin Oncol, 119: 507-510 (1993).
Wahdi, MM. et al., Evidence for the treatment of patients with pulmonary nodules: when is it lung cancer? ACCP evidence-based clinical practice guidelines 2nd Edition, Chest 2007; 132:94-107S (2007).
West, M., et al. Embracing the complexity of genomic data for personalized medicine, Genome Res 2006; 16:559-66 (2006).
Wistuba, et al., Molecular damage in the bronchial epithelium of current and former smokers. J Natl Cancer Inst., 89(18): 1366-73 (Sep. 17, 1997).
Wistuba, et al., High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).
Zeeberg, et al.. GoMiner: a resource for biological interpretation of genomic and proteomic data. Genome Biology, 4(4):R28.1-R28.8 (2003).
Zhang, et al. Comparison of smoking-induced gene expression on Affymetrix Exon and 3'-based expression arrays. Genome Inform. 18: 247-57 (2007).
Retracted in Jan. 2011—Potti, A., et al., "Genomic Signatures to Guide the Use of Chemotherapeutics," Nature Medicine, 12(11): 1294-1300 (2006).
Ambion, Inc. "GeneAssist Pathway Atlas for P13K Signaling," Accessed from http://www5.aapliedbiosystems.com/tools/pathway/pathway_proteins.php?pathway=P13K on May 3, 2011.
Arimura, et al. Elevated Serum β-Defensins Concentrations in Patients with Lung Cancer, Anticancer Research, 24: 4051-4058 (2004).
Baker, Stuart. "The Central Role of Receiver Operating Characteristic (ROC) Curves in Evaluating Tests for the Early Detection of Cancer," Journal of the National Cancer Institute, 95(7): 511-515 (2003).
Braakhuis, et al. "A Genetic Explanation of Slaughter's Concept of Field Cancerization Evidence and Clinical Implications," Cancer Research, 63: 1727-1730 (2003).
Chan, et al. Intefrating Trasnscriptomics and Protemoics, Genomics & Proteomics Magazine, 6(3), text of article reprinted and accessed from www.dddmag.com on May 27, 2005.
Chen, et al. "Discordant Protein and mRNA Expression in Lung Adenocarcinomas," Molecular and Cellular Proteomics, 1: 304-313 (2001).
Dauletbaev, et al. "Expression of Human Beta Defensin (HBD-1 and HBD-2) mRNA in Nasal Epithelia of Adult Cystic Fibrosis Patients, Healthy Individuals, and Individuals with Acute Cold," Respiration, 69:46-51 (2002).
Franklin, et al. "Widely Dispersed p53 Mutation in Respiratory Epithelium," The Journal of Clinical Investigation, 100(8): 2133-2137 (1997).
Hellmann, et al. "Gene Profiling of Cultured Human Bronchia Epithelial and Lung Cacinoma Cells," Toxicological Sciences, 61: 154-163 (2001).
Ikeda, et al. "Malignancy associated changes in bronchial epithelial cells and clinical application as a biomarker," Lung Cancer, 19(3): 161-166 (1998).
Kraft, et al. "Expression of epithelial markers in nocturnal asthma," Journal of Allergy and Clinical Immunology, 102(3): 376-381 (1998).
Liu, et al. "Quantitative Proteome Analysis Reveals Annexin A3 as a Novel Biomarker in Lung Adenocarcinoma," Journal of Pathology, 217: 54-64 (2009).
Reynolds, et al. "Pre-protachykinin-A mRNA is increased in the airway epithelium of smokers with chronic bronchitis." Respiratory, 6:187-197 (2001).
Riise, et al. "Bronchial Brush Biopsies for Studies of Epithelial Inflammation in Stable Asthma and Nonobstructive Chronic Bronchitis," European Respiratory Journal, 9: 1665-1671 (1996).
Slonim, Donna. "From Patterns to Pathways: Gene Expression Data Analysis Comes of Age," Nature Genetics Supplement, 32: 502-508 (2002).
Takizawa, et al. "Increased expression of transforming growth factor-beta1 in small airway epithelium from tobacco smokers and patients with chronic obstructive pulmonary disease (COPD)," American Journal of Respiratory and Critical Care Medicine, 163:1476-1483 (2001).
Watters, et al. "Developing Gene Expression Signatures of Pathway Deregulation in Tumors," Molecular Cancer Therapeutics, 5: 2444-2449 (2006).
Ohtsuka, et al., Ohtsuka, et al., "ADAM28 is overexpressed in human non-small cell lung carcinomas and correlates with cell proliferation and lymph node metastasis," International Journal of Cancer, 118(2): 263-273 (2006).
Hamilton and Sharp, "Diagnosis of lung cancer in primary care: a structured review," Family Practice, 21(6), 605-611 (2004).
Akita, et al., "Molecular Biology of Lung Cancer," The Journal of the Japanese Respiratory Society, 42(5): (2004).
Printout from database NCBI GEO accession No. GSE4115 [Online] NCB, dated Feb. 27, 2006.

(56) References Cited

OTHER PUBLICATIONS

Brody, Jerome S., Abstract "Airway epithelial gene expression in COPD" National Institutes of Health Grant No. 1 R01 HL071771-01 (Funding Start Date Sep. 30, 2002).
Kiss, et al., "Anatomisk Atlas over Manniskokroppen, band II," Natur och Kultur Stockholm, Stockholm, Sweden ISBN: 91-27-67278-6 (1973).
Bohula et al., "The Efficacy of Small Interfering RNAs Targeted to the Type 1 Insulin-like Growth Factor Receptor (IGF1R) Is Influenced by Secondary Structure in the IGF1R Transcript," The Journal of Biological Chemistry 278(18): 15991-15997 (2003).
Wardlaw, et al., "Effect of cigarette smoke on CYP1A1, CYP1A2 and CYP2B1/2 of nasal mucosae in F344 rats," Carcinogenesis 19(4): 655-662 (1998).
Lin, et al., "Effects of Dexamethasone on Acute Lung Injury Rat Cells Signal Transduction Systems ERK and PI3-K," Medical Journal of Chinese People's Liberation Army 6(31): 592-594 (2006).
Guajardo, et al., "Altered gene expression profiles in nasal respiratory epithelium reflect stable versus actue childhood asthma", J. Allergy Clin Immunol 115(2): 243-251 (2005).
Voynow, et al., "Mucin Gene Expression (MUC1, MUC2, and MUC5/5AC) in Nasal Epithelial Cells of Cystic Fibrosis, Allergic Rhinitis, and Normal Individuals", Lung 176: 345-354 (1998).
Shah et al., "SIEGE: Smoking Induced Pithelial Gene Expression Database", Nucleic Acids Research, 33: D573-D579 (2005).
Enard et al., "Intra- and Interspecific Variation in Primate Gene Expression Patterns", Science 296: 340-343 (2002).
Cheung, et al., "Natural variation in human gene expression assessed in lymphoblastiod cells", Nature Genetics, 33: 422-425 (2003).
Wu, Thomas D., "Analysing gene expression data from DNA microarrays to identify candidate genes", Journal of Pathology, 195:53-65 (2001).
Newton, et al., "On Differential Variability of Expression Ratios: Improving Statistical Inference about Gene Expression Changes from Microarray Data", Journal of Computational Biology, 8: 37-52 (2001).
Fritz, et al., "Nasal mucosal gene expression in patients with allergic rhinitis with and without nasal polyps", Journal of Allergy Clin. Immunol, 112(6): 1057-1063 (2003).
Lam, et al., "A Phase I Study of myo-Inositol for Lung Cancer Chemoprevention", Cancer Epidemiology, Biomarkers & Prevention 15(8): 1526-1531 (2006).
Peluso, et al., "Comparison of DNA adduct levels in nasal mucosa, lymphocytes and bronchial mucosa of cigarette smokers and interaction with metabolic gene polymorphisms", Carcinogenesis 25(12): 2459-2465 (2004).
Marinov, et al., "Targeting mTOR signaling in lung cancer", Critical Reviews in Oncology/Hematology 63: 172-182 (2007).
Singhal, et al., "Alterations in Cell Cycle Genes in Early Stage Lung Adenocarcinoma Identified by Expression Profiling", Cancer Biology & Therapy 2(3): 291-299 (2003).
Danel, et al., "Quantitative assessment of the epithelial and inflammatory cell populations in large airways of normal and individuals with cystic fibrosis," American Journal of Respiratory and Critical Care Medicine 153(1): 362-368 (1996).
Merriam-Webster.com (htpp://www.merriam-webster.com/dictionary/questionnaire, downloaded Oct. 26, 2013).
Tarca, et al., "Analysis of microarray experiments of gene expression profiling," American Journal of Obstetrics and Gynecology 195(2): 373-388 (2006).
May, "How many species are there on earth?" Science 241(4872): 1441-1449 (1988).
Benner, et al. "Evolution, language and analogy in functional genomics," Trends in Genetics 17(7): 414-418 (2001).
Modrek, et al., "Genome-wide detection of alternative splicing in expressed sequences of human genes," Nucleic Acids Research 29(13): 2850-2859 (2001).
Woenckhaus, et al., "Smoking and cancer-related gene expression in bronchial epthelium and non-small-cell lung cancers," The Journal of Pathology 210(2): 192-204 (2006).

Details for HG-U133A:202831_AT (https://www.affymetrix.com/analysis/netaffx/fullrecord.affx?pk=HG-U133A:202831_AT, downloaded Dec. 10, 2012).
Details for HG-U133A:210519_S_AT (https://www.affymetrix.com/analysis/netaffx/fullrecord.affx?pk=HG-U133A:210519_S_AT downloaded Dec. 10, 2012).
HG-U133a-207469_S_AT (https:www/affymetrix.com/analysis/netaffx/fullrecord.affx?pk= HG-U133A:207469_S_AT, downloaded Dec. 10, 2012.
HG-U133A:823_AT (https://www.affymetrix.com/analysis/netaffx/fullrecord.affx?pk=HG-U133A:823_AT, downloaded Dec. 10, 2012.
Demoly, et al., "c-fos Proto-oncogene Expression in Bronchial Biopsies of Asthmatics," American Journal of Respiratory Cell and Molecular Biology 7:128-133 (1992).
Hennessy, et al., "Exploiting the PI3K/AKT Pathway for Cancer Drug Discovery," Nature, vol. 4: 988-1004 (2005).
Langford, et al., "Is the Property of Being Positively Correlated Transitive," The American Statistician 55(4): 322-325 (2001).
Saal, et al., "Poor Prognosis in Carcinoma is Associated with a Gene Expression Signature of Aberrant PTEN Tumor Suppressor Pathway Activitiy," PNAS 104(18): 7564-7569 (2007).
Sotos, et al., "The Transitivity Misconception of Pearson's Correlation Coefficient," Statistics Education Research Journal 8(2): 33-55 (2009).
Ronald A. Thisted, "What is a P-value", Departments of Statistics and Health Studies, The University of Chicago, May 25, 1988.
Tichelaar, et al., "Increased Staining for Phospho-Akt, p65/RELA and cIAP-2 in Pre-neoplastic Human Bronchial Biopsies," BMC Cancer 5(155): 1-13 (2005).
Tsao, et al, "Increased Phospho-AKT (Ser$^{473}$) Expression in Bronchial Dysplasia: Implications for Lunch Cancer Prevention Studies," Cancer, Epidemiology, Biomarkers & Prevention 12:660-664 (2003).
West, et al, "Rapid Akt Activation by Nicotine and Tobacco Carcinogen Modulates the Phenotype of Normal Human Airway Epithelial Cells," The Journal of Clinical Investigation 111(1): 81-90 (2003).
Hoshikawa, et al., "Hypoxia induces difference genes in the lungs of rats compared with mice," Physiol Genomics 12: 209-219 (2003).
Cheng, et al., "Reduced expression levels of nucleotide excision repair genes in lung cancer: a case-control analysis," Carcinogenesis 21(8): 1527-1530 (2000).
Fielding, et al., "Heterogeneous Nuclear Ribonucleoprotein A2/B1 Up-Regulation in Bronchial Lavage Specimens: A Clinical Marker of Early Lung Cancer Detection," Clinical Cancer Research 5:4048-4052 (1999).
Yu-Rong, et al., "Tumor associated antigen L6 and the invasion of human lung cancer cells." Clinical Cancer Research 9(7): 2807-16 (2003).
Dempsey, et al., "Lung disease and PKCs," Pharmacological Research 55(6): 545-59 (2007).
MacKay et al., "Targeting the protein kinase C family: are we there yet?" Nature Reviews Cancer 7(7): 554-62 (2007).
Gustafson, et al., "Airway P13K Pathway Activation Is an Early and Reversible Even in Lung Cancer Development," www.ScienceTransmlationMedicine.org 2(26) (2010).
Fukumoto, et al., "Overexpression of the Aldo-Keto Reductase Family Protein AKR1B10 is Highly Correlated with Smokers' Non-Small Cell Lung Carcinomas," Clinical Cancer Research 11:1776-1786 (2005).
Whitehead et al., "Variation in tissue-specific gene expression among natural populations," Genome Biology 6(2):R13.1-R13.14 (2005).
European Search Report in Application EP 10 19 5822, dated Jun. 20, 2011.
European Search Report in Application EP 10 19 5803, dated Jun. 20, 2011.
European Search Report in Application EP 10 18 4732, dated Mar. 21, 2011.
European Search Report in Application EP 10 18 4813, dated Mar. 21, 2011.

(56) References Cited

OTHER PUBLICATIONS

European Search Report in Application EP 10 18 4888, dated Mar. 21, 2011.
European Search Report in Application EP 04 81 0818, dated Oct. 28, 2010.
European Search Report in Application EP 08 83 2403, dated Oct. 22, 2010.
European Search Report in Application EP 09 72 4548, dated Jun. 16, 2011.
European Search Report for European Application No. EP 10195816, dated Oct. 13, 2011.
European Search Report in Application EP 12 17 0635, dated Apr. 22, 2013.
Chinese Search Report in Application 2008801147951 dated Aug. 24, 2012.
Non-Final Office Action for U.S. Appl. No. 12/234,588, dated Jun. 27, 2011.
Non-Final Office Action for U.S. Appl. No. 10/579,376, dated Jul. 9, 2008.
Non-Final Office Action for U.S. Appl. No. 11/294,834, dated Jun. 24, 2008.
Non-Final Office Action for U.S. Appl. No. 12/884,714, dated Sep. 23, 2011.
Final Office Action for U.S. Appl. No. 12/234,588, dated Nov. 4, 2011.
Non-Final Office Action for U.S. Appl. No. 12/414,555, dated Nov. 30, 2011.
Final Office Action for U.S. Appl. No. 12/414,555, dated Mar. 15, 2012.
Non-Final Office Action for U.S. Appl. No. 13/323,655 dated Apr. 9, 2013.
Non-Final Office Action for U.S. Appl. No. 13/524,749, dated Sep. 9, 2013.
Non-Final Office Action for U.S. Appl. No. 12/234,588, dated Mar. 28, 2014.
Final Office Action for U.S. Appl. No. 13/524,749, dated Apr. 3, 2014.
Final Office Action for U.S. Appl. No. 13/323,655, dated Jul. 17, 2014.
Final Office Action for U.S. Appl. No. 11/294,834, dated Aug. 18, 2014.
Final Office Action for U.S. Appl. No. 13/346,444, dated Nov. 27, 2013.
Non-Final Office Action for U.S. Appl. No. 11/294,834, dated Jan. 29, 2014.
Non-Final Office Action for U.S. Appl. No. 13/346,444, dated Dec. 12, 2012.
Non-Final Office Action for U.S. Appl. No. 13/323,655, dated Nov. 7, 2013.
Non-Final Office Action for U.S. Appl. No. 11/294,834, dated Jul. 29, 2014.
Non-Final Office Action for U.S. Appl. No. 11/294,834, dated Dec. 15, 2015.
Anbazhagan, et al., "Classification of Small Cell Lng Cancer and Pulmonary Carcinoid by Gene Expression Profiles," *Cancer Research*, 59:5119-5122, (Oct. 15, 1999).
Chen, et al., "Up-regulations of Tumor Interleukin-8 Expression by Infiltrating Macrophages: Its Correlation with Tumor Angiogenesis and Patient Survival in Non-Small Cell Lung Cancer," *Clinical Cancer Research*: p. 729, (Feb. 1, 2003).
Grepmeier, et al., "Deletions at chromosome 2q and 12p are early frequent molecular alterations in bronchial epithelium and NSCLC of long-term smokers." *Int J Oncol.*, 27(2):481-8(2005).
Khan, et al., "Classification and Diagnostic Prediction of Cancers Using Gene Expression Profiling and Artificial Neural Networks," *Nature Medicine*, 7(6):673-679, (Jun. 2001).
Woenckhaus, et al., "Expression Profiling of Non-Small Cell Lung Cancers and Bronchi of Smokers and Non Smokers," *Study Group: Molecular Pathology/Pathology—Research and Practice*, 200:p. 255, (2004).

Extended European Search Report from EP 16186152.1, dated May 31, 2017.
Final Office Action for U.S. Appl. No. 14/613,210, dated Apr. 3, 2017.
Vartiainen, et al., "Validation of Self-Reported Smoking by Serum Cotinine Measurement in a Community-Based Study," *J. Epidemiol Community Health*, 56:167-170, (2002).
Zhang, et al., "Similarities and Differences Between Smoking-Related Gene Expression in Nasal and Bronchial Epithelium," *Physiol. Genomics*, 41:1-8, (2010).
Final Office Action for U.S. Appl. No. 15/336,469, dated Oct. 9, 2018).
Final Office Action for U.S. Appl. No. 14/690,182, dated Oct. 9, 2018.
Yoneda, et al., "Development of High-Density DNA Microarray Membrane for Profiling Smoke- and Hydrogen Peroxide-Induced Genes in a Human Bronchial Epithelial Cell Line," *American Journal of Respiratory and Critical Care Medicine*, 164:S86-S89, (2001).
International Search Report for PCT/US2017/032517, dated Oct. 2, 2017.
Notice of Allowance for U.S. Appl. No. 14/613,210, dated Oct. 31, 2017.
Beane-Ebel, "Single-Cell RNA Sequenceing of the Bronchial Epithelium in Smokers With Lung Cancer," U.S. Army Medical Research and Material Command. Jul. 1, 2016 [retrieved on Sep. 19, 2017]. Retrieved from the Internet at http://www.dtic.mil/dtic/tr/fulltext/u2/a624219.pdf.
Durham, et al., "The Relationship Between COPD and Lung Cancer," *Lung Cancer*, 90:121-127, (2015).
Kocarnik, et al., "Replication of Associations Between GWAS SNPs and Melanoma Risk in the Population Architecture Using Genomics and Epidemiology (PAGE) Study," *Journal of Investigative Dermatology*, 134:2049-2052, (Feb. 27, 2014).
Notterman, et al., "Tumor Biology and Microarray Analysis of Solid Tumors: Colorectal Cancer as a Model System," *Microarrays and Cancer Research*, Warrington et al (eds.), Eaton Publishing, Westborough, MA, pp. xi-xvi, (2002).
Ooi, et al., "Molecular Profiling of Premalignant Lesions in Lung Squamous Cell Carcinomas Identifies Mechanisms Involved in Stepwise Carcinogenesis," *Cancer Prevention Research*, 7(5):487-495, (Mar. 11, 2014).
Strausberg, et al., "Reading the Molecular Signatures of Cancer," *Microarrays and Cancer Research*, Warrington et al. (eds.), Eaton Publishing, Westborough, MA, pp. 81-111, (2002).
International Search Report for PCT/US2017/041267, dated Dec. 15, 2017.
Non-Final Office Action for U.S. Appl. No. 15/644,721, dated Dec. 27, 2017.
Coleman, "Of Mouse and Man—What is the Value of the Mouse in Predicting Gene Expression in Humans?" *Drug Discovery Today*, 8(6):233-235, (Mar. 2003).
Cooper, "Gene Expression Studies in Lung Cancer," *The Molecular Genetics of Lung Cancer*, pp. 167-186, (2005).
Deng, et al., "Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase," *Cancer Chemother. Pharmacol.*, 54:301-307, (2004).
Kuriakose, et al., "Selection and Validation of Differentially Expressed Genes in Head and Neck Cancer," *CMLS*, 61:1372-1383, (2004).
Su, et al. "Molecular Classification of Human Carcinomas by Use of Gene Expression Signatures," *Cancer Research*, 61:7388-7393, (Oct. 15, 2001).
Sugita, et al., "Combined Use of Oligonucleotide and Tissue Microarrays Identifies Cancer/Testis Antigens as Biomarkers in Lung Carcinoma," *Cancer Research*, 62:3971-3979, (Jul. 15, 2002).
Yang, et al., "Reduction of Dihydrodiol Dehydrogenase Expression in Resected Hepatocellular Carcinoma," *Oncol. Rep.*, 10(2):271-276, Abstract pp. 1-2 (2003).
Zochbauer-Muller, et al., "5' CpG Island Methylation of the FHIT Gene is Correlated with Loss of Gene Expression in Lung and Breast," *Cancer Research*, 61:3581-3585, (May 2, 2001).

(56) References Cited

OTHER PUBLICATIONS

European Search Report for European Application No. EP 17185133.0, dated Feb. 21, 2018.
Final Office Action for U.S. Appl. No. 15/439,891, dated Feb. 14, 2018.
Non-Final Office Action for U.S. Appl. No. 14/690,182, dated Apr. 20, 2018.
Non-Final Office Action for U.S. Appl. No. 15/888,831, dated Mar. 27, 2018.
Non-Final Office Action for U.S. Appl. No. 15/336,469, dated Apr. 10, 2018.
Final Office Action for U.S. Appl. No. 15/888,831, dated Jul. 24, 2018.

* cited by examiner

METHODS OF IDENTIFYING INDIVIDUALS AT INCREASED RISK OF LUNG CANCER

RELATED APPLICATIONS

This application is a continuation of U.S. application Ser. No. 12/234,588, filed on Sep. 19, 2008, which claims the benefit of U.S. provisional application Ser. No. 60/994,643, filed Sep. 19, 2007, the entire teachings of which are incorporated herein by reference.

GOVERNMENT SUPPORT

The invention was made with government support under Grant Nos. NIH/NCI R01CA124640 and NIH/NCI CA106506 awarded by the National Cancer Institute at the National Institutes of Health. The government has certain rights in the invention.

BACKGROUND OF THE INVENTION

Cigarette smoke is the dominant cause of lung cancer in the United States, accounting for an estimated 90% of all cases [1]. However, the damage caused by cigarette smoke is not limited solely to the lung, but rather constitutes a 'field of injury' throughout the entire respiratory tract [2-6]. An important product of the field of injury hypothesis is the ability to glean clinically relevant information from cells collected in regions of the respiratory tract, such as the bronchial airway, that can be obtained in a less invasive manner than is typical of collecting primary lung tissue. Based on this approach, a gene expression-based biomarker measured in the cytologically normal bronchial airway epithelium that can distinguish smokers with and without lung cancer has been developed [7]. This airway gene expression biomarker achieved 83% accuracy in predicting whether a smoker had a lung tumor in a prospective test set, and 94% accuracy when combined synergistically with clinical variables [7, 8].

Beyond serving as an early diagnostic tool for lung cancer, gene expression changes in the cytologically normal airway epithelium have the potential to improve our understanding of the signaling events deregulated during early stages of lung cancer. Lung cancer development in humans is a complex process involving multiple aberrant events that, when accumulated, lead to deregulation of crucial cell functions, including cell survival and proliferation. In primary tumors resected from patients with lung cancer, many signaling pathways have previously been found to be deregulated, such as p53, RAS and phosphatidylinositol 3-kinase (PI3K) [9-11]. Additionally, studies in the field of injury and field cancerization have found that some of the molecular changes presumed to be early in tumorigenesis are also reflected in histologically normal cells both neighboring and more distal to the primary tumor. For example, the same p53 mutation or loss of heterozygosity at a specific chromosomal region have been identified throughout the entire respiratory tract [5, 12].

Insight into the deregulation of oncogenic pathways in cytologically normal bronchial airway cells from smokers with lung cancer will help elucidate mechanisms involved in the progression into malignancy. Furthermore, understanding which pathways are deregulated could lead to therapeutic and chemoprophylactic opportunities at the pre-malignant stage of lung cancer.

SUMMARY OF THE INVENTION

It has been previously demonstrated that gene expression profiling of cytologically normal bronchial airway epithelium reflects a field of injury in smokers that can serve as a sensitive and specific diagnostic biomarker for lung cancer. Using gene expression signatures defined by in vitro perturbation of specific oncogenic pathways, as described herein a significant increase of phosphatidylinositol 3-kinase (PI3K) pathway activity was identified in the cytologically normal airway of smokers with lung cancer (n=129), as well as in lung tumor tissue (n=107). To evaluate whether increased activity of PI3K occurs prior to the development of lung cancer, cytologically normal airway epithelia in high-risk smokers with moderate-severe dysplastic lesions in their airway (n=14) were profiled, and higher levels of PI3K pathway gene expression were found as compared to the airway epithelium from healthy smokers without dysplasia (n=11). Further, PI3K activity was decreased in the airway of high-risk smokers who had significant regression of dysplasia following treatment with the chemoprophylactic agent myo-inositol (n=10). In vitro dilution experiments confirmed that myo-inositol inhibits the PI3K pathway, which not only proposes a mechanism of action for myo-inositol, but also reflects a potential therapeutic relationship between PI3K pathway activity and regression of airway dysplasia. Together, these findings suggest that deregulation of the PI3K pathway is an early, measurable and reversible step in the development of lung cancer, and that airway gene expression profiling in smokers may enable personalized approaches to chemoprophylaxis and therapy.

In one embodiment the invention provides biomarkers for oncogenic pathways activated in cytologically normal airway epithelial cells of individuals with lung disease. These biomarkers and pathways may provide prognostic and/or diagnostic indicators of lung disease, e.g., lung cancer. Additionally, these pathways and biomarkers may provide therapeutic targets for the treatment of lung disease, as well as markers for the assessment of treatment efficacy.

In one aspect the invention relates to the use of gene expression profiling methods to identify gene expression signatures of oncogenic pathways activated in lung disease, e.g., lung cancer. These gene expression signatures may provide prognostic or diagnostic indicators for lung disease, e.g., lung cancer. Moreover, oncogenic pathways which are activated in lung disease may be targets for therapeutic intervention. In one embodiment the oncogenic pathway can be, for example, one or more of the PI3K and Np63 pathways.

The invention also relates to a method of identifying an individual at increased risk of lung disease, comprising determining the activation status of the Np63 and/or PI3K pathway in a cytologically normal airway epithelial cell from said individual, wherein activation of the Np63 and/or PI3K pathway is indicative that said individual is at increased risk of lung disease as compared with an individual in whom the Np63 and/or PI3K pathway is not activated. In particular embodiments the individual is a smoker or a non-smoker. In other embodiments the lung disease is lung cancer.

In one embodiment the activation status of the PI3K pathway is determined using gene expression data for one or more biomarkers of the PI3K pathway. For example, in some embodiments at least one of said one or more biomarkers is a gene which is increased upon PI3K activation, and in other embodiments at least one of said one or more biomarkers is a gene which is decreased upon PI3K activation. Combinations of biomarkers which are increased and decreased upon PI3K activation may also be used. In particular embodiments at least one of said one or more biomarkers is a gene which is upstream of PI3K activation, while in other embodiments at least one of said one or more biomarkers is a gene which is downstream of PI3K activation.

In particular embodiments, expression data for said one or more biomarkers of the PI3K pathway is obtained using an oligonucleotide microarray. In other embodiments the activation status of the PI3K pathway is determined using one or more gene expression products of one or more biomarkers of the PI3K pathway. Said gene expression products may be nucleotide or amino acid products and can be detected using methods known in the art.

In some embodiments of the invention the activation status of the PI3K pathway is determined by assessing the activation of IGF1R, wherein activation of IGF1R is indicative of activation of the PI3K pathway. In other embodiments of the invention the activation status of the PI3K pathway is determined by assessing the activation of PKC, wherein activation of PKC is indicative of activation of the PI3K pathway.

The invention also relates to a method of identifying an individual at increased risk of lung disease, comprising determining the activation status of PKC in a cytologically normal airway epithelial cell from said individual, wherein activation of PKC is indicative that said individual is at increased risk of lung disease as compared with an individual in whom PKC is not activated.

The invention further relates to a method of identifying an individual at increased risk of lung disease, comprising determining the activation status of IGF1R in a cytologically normal airway epithelial cell from said individual, wherein activation of IGF1R is indicative that said individual is at increased risk of lung disease as compared with an individual in whom IGF1R is not activated.

In other embodiments the invention provides an oligonucleotide array having immobilized thereon one or more probes for one or more biomarkers of the PI3K pathway, and wherein said array does not have immobilized thereon probes for other biomarkers. In preferred embodiments said one or more biomarkers of the PI3K pathway are selected from the group consisting of IGF1R, PKC, the biomarkers disclosed in [29], and combinations thereof.

The invention also relates to a method of reducing the risk of lung disease in an individual comprising administering to an individual at risk of lung disease one or more agents (e.g., one or more agents, regimens or treatments or combinations thereof) which inhibit the PI3K pathway. In particular embodiments the PI3K pathway is activated in said individual prior to administration of said one or more agents. In one embodiment the lung disease is lung cancer. In another embodiment said one or more agents are administered to said individual prophylactically before the development of lung disease.

In another embodiment the invention relates to a method of differentially classifying a cytologically normal test airway epithelial cell, comprising identifying a gene expression signature associated with activation of a biological pathway of interest in a normal airway epithelial cell; assessing gene expression in differentially classified airway epithelial cells to identify one or more correlations between classification of an airway epithelial cell and activation of a biological pathway of interest; and assessing gene expression in a cytologically normal test airway epithelial cell, wherein the gene expression profile of the cytologically normal airway epithelial cell to be classified indicates whether the biological pathway of interest is activated and thus differentially classifies the cell.

In particular embodiments the biological pathway of interest is an oncogenic pathway. In some embodiments the differential classification is increased risk of disease versus decreased risk of disease, while in other embodiments the differential classification is response to treatment versus non-response to treatment.

In one embodiment, the invention provides a method for identifying the activation of an oncogenic pathway in a mammal having or at risk of having lung disease, e.g., lung cancer. The method may include: (a) providing a biological sample, e.g., a biological sample from an airway passage of the mammal, wherein the biological sample comprises a gene expression product (e.g., mRNA or protein) from at least one gene that is indicative of activation of said pathway, and (b) detecting the expression of said gene. For example, the pathway can be one or more of the following: Ras, Myc, E2F3, beta-catenin, Src, Np63, PI3K and combinations thereof. The mammal can be, for example, a human. Biological samples may be provided, for example, from bronchial, nasal or buccal epithelium, or from biopsied tissue samples. In one embodiment, detection of gene expression is accomplished using an oligonucleotide array having immobilized thereon one or more nucleotide sequences or fragments thereof which are probes for the relevant gene(s). Identification of activation of an oncogenic pathway may indicate that the mammal is a candidate for treatment to inhibit activation of said pathway or for additional or more frequent screening to identify development of disease, e.g., cancer.

In another embodiment, the invention provides a method of screening candidate therapeutic agents which may be useful in the treatment of lung disease, e.g., lung cancer. For example, candidate agents may be screened for their ability to modulate (e.g., inhibit) the activation of an oncogenic pathway identified by methods described herein as associated with lung disease. The agent's ability to modulate activation of the pathway may be assessed, for example, by its ability to alter a gene expression signature of an oncogenic pathway from a signature which is associated with disease to a signature which is not associated with disease, e.g., is normal. Alternatively the candidate therapeutic agent may be assessed for its ability to modulate a specific functional effect or readout of the pathway. Agents identified as having the ability to inhibit an activated oncogenic pathway associated with lung disease may be suitable for treatment of lung disease in a mammal.

In addition, the efficacy of a treatment regimen can be evaluated by assessing the gene expression signature of a mammal at various time points over the course of treatment. A shift in the gene expression signature of an oncogenic pathway from one associated with disease to one not associated with disease, e.g., to a normal signature, is indicative of efficacious treatment. Similarly absence of a shift in the gene expression signature toward a normal signature is indicative that treatment is not efficacious and that perhaps alternative treatment regimens are indicated.

BRIEF DESCRIPTION OF THE DRAWINGS

As shown in FIG. 1A, when grouping the activation levels by lung cancer status (blue for no lung cancer, red for lung cancer), two pathways were found to be statistically different after random permutation tests: PI3K (p<0.001), and ΔNp63 (p<0.001). To account for variables that could possibly confound the observed differences in pathway activation seen in the airway of smokers with lung cancer, pathway activation probabilities were also calculated for healthy never (green), former (brown) and current smokers (gray) (FIG. 1B), as well as current smokers with (orange) or without (gray) chronic obstructive pulmonary disease (COPD) (FIG. 1C). Neither of the potential confounding variables showed a statistically significant difference in pathway activation.

As shown in FIG. 3A, kinase assays were used to measure in vivo levels of PI3K pathway activity. Patients with lung cancer generally had higher levels of PI3K activity than those without lung cancer. A subset of the Boston cohort had extra sample run on microarray so that computational predicted PI3K activity could be correlated to in vivo activity. The probability of pathway activity is shown below the patients that had extra samples. Pearson correlation of the computationally predicted PI3K activity and the biochemically measured activity was 0.48. As shown in FIG. 3B, Western blots querying proteins both upstream and downstream of PI3K were quantified and then correlated with PI3K kinase levels measured in FIG. 3A. Correlations are presented in a heatmap manner, where blue represents negative correlation, and red represents positive correlation. Correlation analysis is also broken down into all samples, only samples with lung cancer, and only control samples. Both p-IGF1R and p-PKC are positively correlated with PI3K activity in patients with lung cancer, suggesting possible sub-pathways driving the increased PI3K pathway activity in the airway of smokers with lung cancer.

(FIG. 5A) BEAS-2B (bronchial airway cell line), (FIG. 5B) BT549 (breast cancer cell line), and (FIG. 5C) HEK293 (human embryonic kidney cell line). The cell lines were then treated with varying doses of myo-inositol and LY-294002. PIP3 levels were measured to quantify the activation levels of the PI3K pathway (y-axis). In each cell line tested, there was a drop in PIP3 levels following treatment with either myo-inositol or LY-294002 (a known PI3K inhibitor), suggesting that myo-inositol inhibits the PI3K pathway in vitro. Replication of these experiments produced similar results.

DETAILED DESCRIPTION OF THE INVENTION

Figures 1A, 1B, 1C:
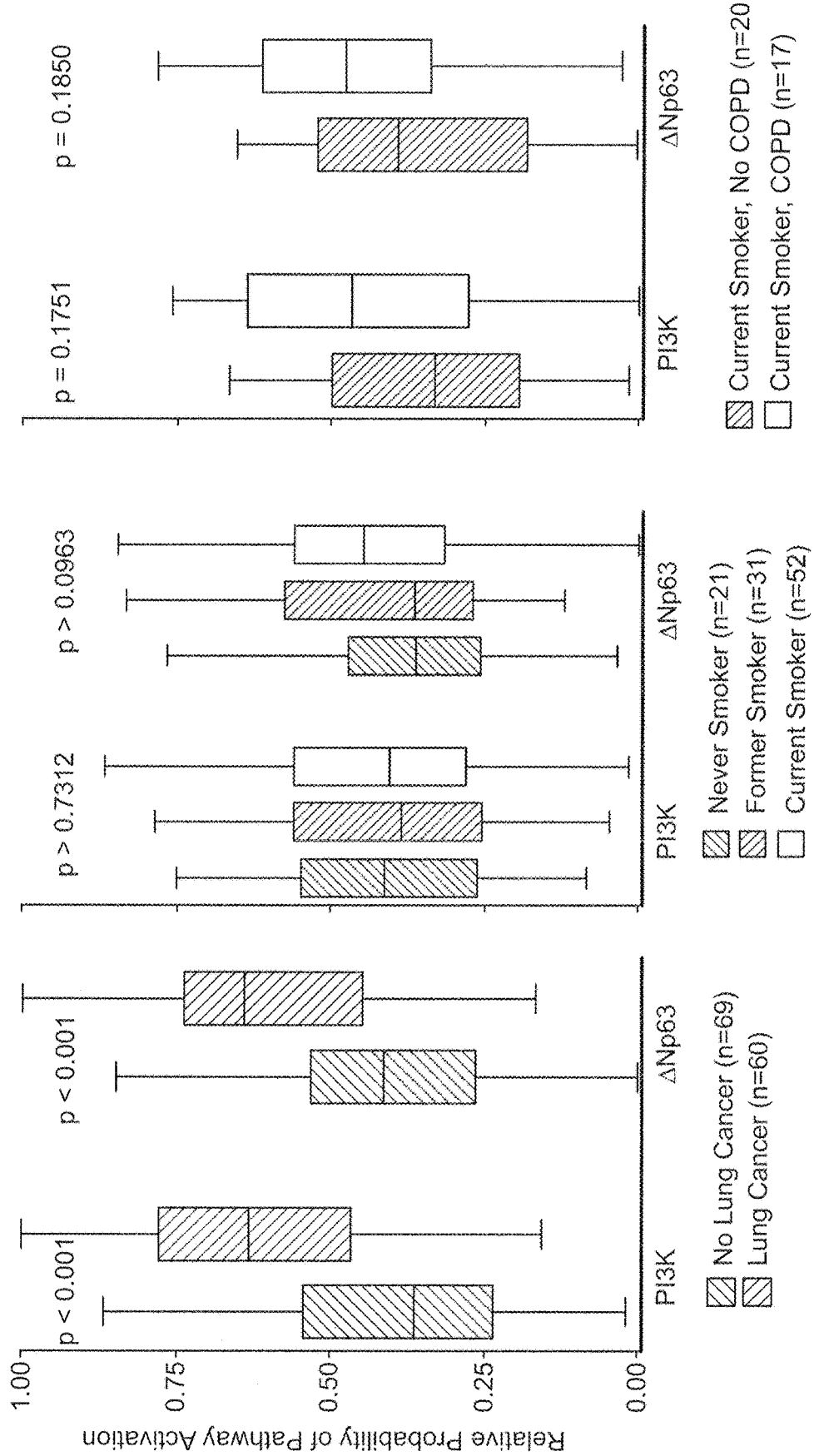
FIGS. 1A-1C show that PI3K and ΔNp63 are differentially activated in smokers with lung cancer. Using binary regression models trained on in vitro gene expression signatures, pathway activation probabilities were calculated in samples obtained from the cytologically normal airway. Pathway levels are summarized using box plots, where the bar represents the median value, the box denotes the range of the data points from the 25th to 75th percentile, and the whiskers specify the range of the remaining 1st and 4th quartile.

Based on the concept that genomic changes in the epithelial cells that line the entire respiratory tract reflect host response to and damage from cigarette smoke, a better understanding of the early events leading to tumorigenesis may be gained by identifying which pathways are deregulated in the airway of smokers with or at risk for having lung cancer. One approach to assess pathway activity uses gene expression data to link in vitro activation of an isolated signaling pathway to predict status of that pathway in patient samples. This approach has been successful at predicting pathway status in cell lines as well as tumors where the initiation event is known [13]. A strength of in vitro defined pathway signatures is that they are capable of identifying pathway activity at the gene expression level, allowing the measurement of multiple pathways using a single microarray experiment. Further, gene expression based predictions of pathway activity have been found to correlate significantly to drugs that target the specific pathway [13-20]. Numerous studies have also found correlation of predicted pathway status and therapeutic responsiveness in clinical trials with targeted therapies [22-25].

Work described herein utilized expression signatures developed through in vitro perturbation. Metagene models were trained to compare oncogenic pathway activity in the cytologically normal airway epithelium of smokers with and without lung cancer. As described herein, using the gene-expression based pathway approach described above, the data show that the PI3K pathway has an increased level of activity in cytologically normal bronchial airway cells of smokers with lung cancer, as well as higher levels in the lung tumor tissue itself. Biochemical assays measuring in vivo PI3K activity in a prospectively collected cohort of airway samples from patients with and without lung cancer validated the computational predictions. An exploration of the expression profiles from the cytologically normal airway of high-risk smokers with dysplastic lesions in their airway again revealed an increased activity of PI3K. As dysplasia is considered a pre-neoplastic event, this is suggestive that PI3K levels increased before the development of lung cancer. Providing possible therapeutic relevance to this result, high-risk subjects responsive to the chemoprophylactic agent myo-inositol show a significant reduction in PI3K activity and regression of dysplastic lesions. The relationship between myo-inositol and PI3K was further elucidated by showing that myo-inositol inhibits PI3K in vitro.

Together, these results demonstrate that the PI3K pathway is activated in the cytologically normal airway epithelium prior to the development of lung cancer, and the levels of this pathway associate with response to chemoprophylaxis with myo-inositol. More broadly, these findings suggest that airway gene-expression reflects perturbation of specific oncogenic pathways within a smoker, potentially allowing for personalized approaches to chemoprophylaxis and therapy.

PI3K and ΔNp63 pathways have an increased activation in the normal airway of smokers with lung cancer (FIG. 1A). This is an intriguing finding, because a priori cytologically normal cells are not expected to show signs of oncogenic pathway deregulation. Additionally, it is important to note that non-lung cancer controls used as described herein have an extensive range of alternative pathologies that could also impact the PI3K pathway, and are not just healthy volunteers. However, the increased activity is not correlated to smoking status or COPD (FIG. 1B, 1C).

Pre-neoplastic increases in the PI3K pathway were also seen in the cytologically normal airway of high-risk smokers with dysplastic airway lesions when compared to healthy smokers. This supports the hypothesis that PI3K activity is induced prior to the development of lung neoplasms. In addition, there are higher levels of PI3K activity in lung tumors as compared to adjacent normal tissue (FIG. 2), suggesting a further increase in PI3K activity as cells transform.

Previous studies using mouse models of lung adenocarcinoma have shown that PI3K is required for malignant progression in lung cancer, and that inhibition of this pathway blocks tumorigenesis [40]. Increased activity of the PI3K pathway has also previously been observed in many different cancers, including lung cancer [41]. Some of the common causes of deregulation that confer constitutive activation in tumors include a mutation in the tyrosine kinase domain of EGFR; a mutation, deletion or suppression of the tumor suppressor PTEN; increased PI3K gene copy number [42] or a mutation in p110α, the catalytic subunit of PI3K [41].

Figure 3A:
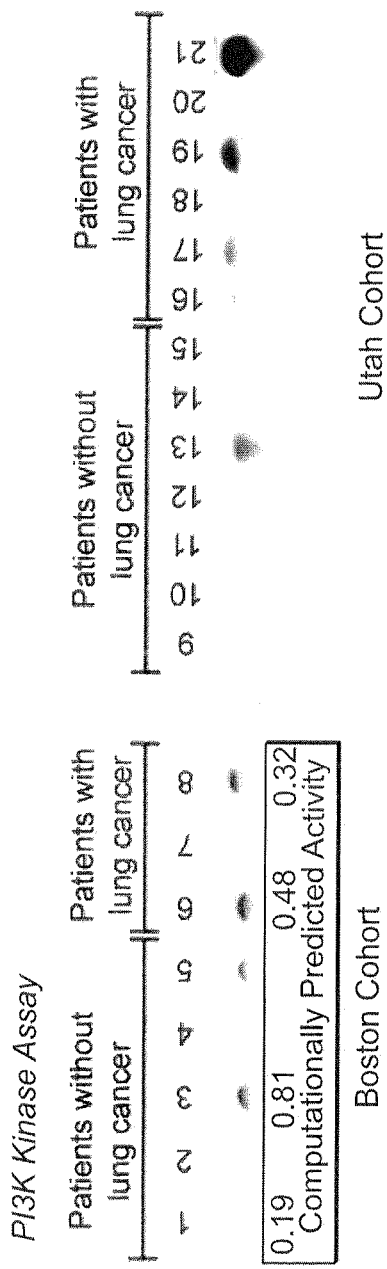
FIGS. 3A-3B show the biochemical validation of PI3K activity in prospectively collected airway samples. Airway brushings were collected prospectively from patients under suspicion of having lung cancer in Boston and Utah.
Figure 3B:
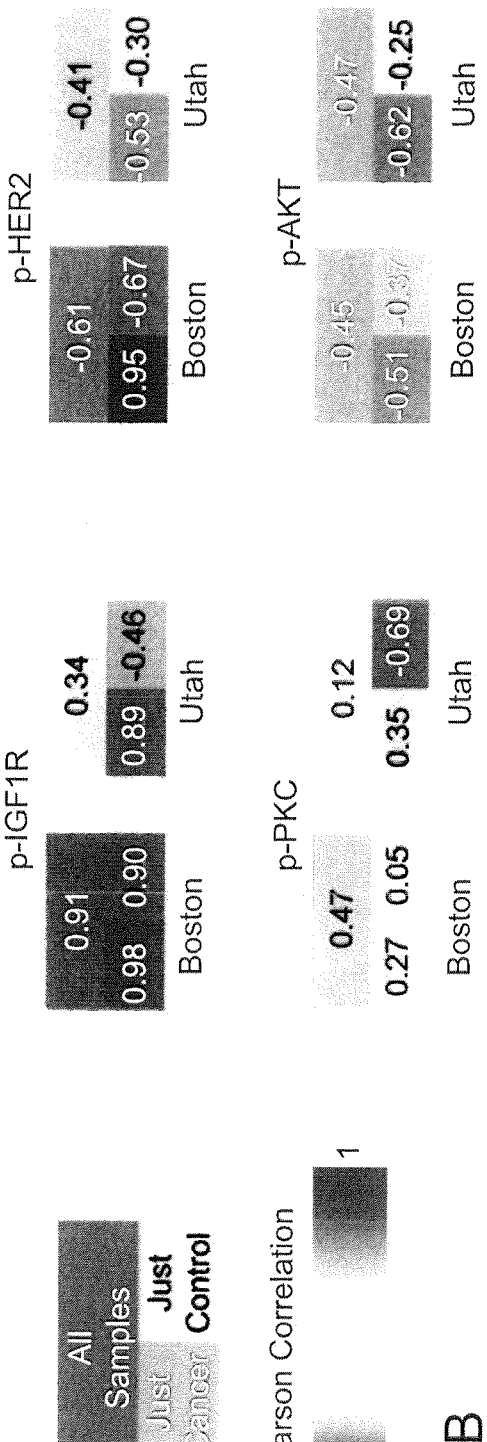
Figure 3B:

In the studies described herein, PI3K activity in the normal airway epithelium of lung cancer patients is positively correlated with activation of IGF1R (upstream) and PKC (downstream), and is not positively correlated with HER2 (upstream) and AKT (downstream) (FIG. 3). These results suggest a specific signaling cascade leading to PI3K activation and subsequent downstream effects in these cells. Increased levels of IGF signaling have been associated with lung cancer in some studies. Further, current inhibitors of the IGF pathway have been found to have significant responses in lung cancer patients. PKC is a kinase downstream of PI3K, and has previously been found to have increased levels in dysplastic lesions and lung cancer [33, 34]. Together, results described herein implicate the IGFR1/PI3K/PKC pathway as central to lung cancer development, even at a pre-malignant state.

Figures 5A, 5B, 5C:
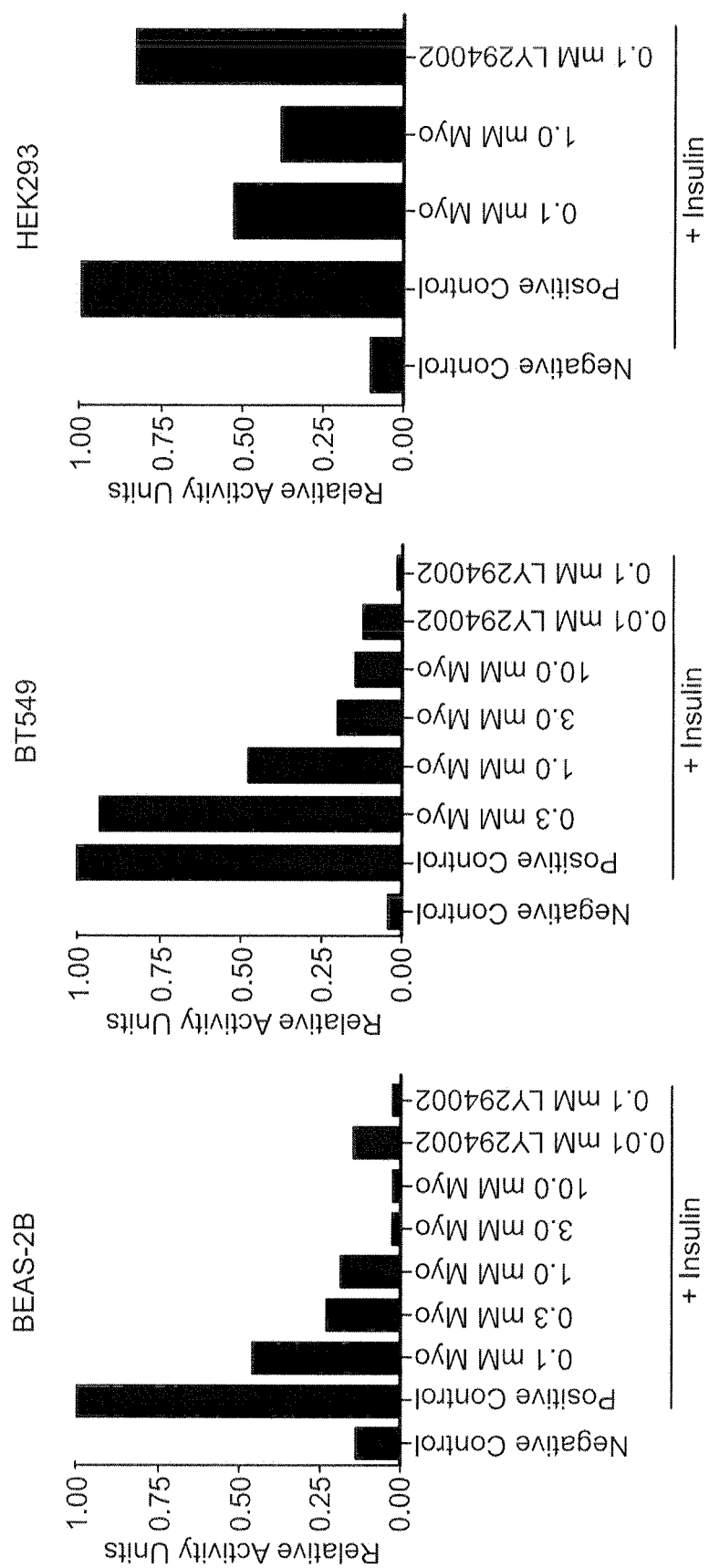
FIG. 5A-5C show that Myo-inositol inhibits the PI3K pathway in vitro. Insulin was used to activate the PI3K pathway in three different cell lines.

Of clinical importance is whether a reduction in PI3K levels prior to the development of lung cancer would offer any therapeutic potential. Current PI3K pathway inhibitors on the market, such as sirolimus, have harmful side effects that would prohibit their use as a long-term prevention option. To help address this crucial question, a study was conducted on a high-risk cohort that had undergone treatment with a lung cancer chemoprophylactic agent called myo-inositol, which has previously been found to reduce dysplastic lesions in the airway following oral treatment for 2-3 months [35]. In contrast to sirolimus, myo-inositol has the potential to be taken orally for long periods of time because it causes very minor side effects. In patients from this cohort that had responded to myo-inositol as evidenced by a regression of dysplasia in their airway, gene expression patterns were observed that reflect a reduction in PI3K activity. Given the relatively limited samples size for this study (n=10), in vitro studies were conducted, and it was found that myo-inositol directly inhibits PI3K activity, suggesting a possible mechanism of action for this compound (FIG. 5). If the chemoprophylactic properties of myo-inositol are confirmed in larger clinical trials, use of this compound in high-risk smokers with perturbed PI3K activity in the airway could decrease lung cancer occurrence. Airway gene expression profiling on these subjects post-treatment may also help identify a subset of patients that would benefit from long-term therapy. More broadly, these results suggest that a smoker's pattern of airway gene-expression reflects perturbation of specific oncogenic pathways, potentially allowing for personalized chemoprophylaxis and therapy.

In principal, there are multiple hypotheses that could explain the increased activity of oncogenic pathways in cytologically normal airway epithelium. Importantly, these concepts are not mutually exclusive and likely work in a synergistic manner to promote disease. First, deregulation could be caused by a genetic predisposition to lung cancer, such as oncogenic germ-line mutations. Second, following the field of injury hypothesis; cigarette smoke exposure damages the entire respiratory tract, and the damage, such as somatic mutations, could be the source of oncogenic activity in the airway. The susceptibility to damage will partly depend on host response to cigarette smoke, which will be influenced by oncogenic germ-line mutations. Finally, somatic mutations conferring growth advantages could cause increased oncogenic activity in the airway due to clonal expansion.

Cumulatively, these studies successfully use a computational approach to identify the signaling pathways driving lung cancer oncogenesis, and to identify rational targeted therapeutic approaches which may be preventative of cancer development in high-risk populations. Further, our biochemical measurements correlate with computational analysis in patient samples, and highlight the specificity and sensitivity of this approach. Verification of pathway activation is also seen in in vitro and in vivo studies linking myo-inositol treatment to inhibition of the PI3K pathway. This suggests that the deregulation of the PI3K pathway is an early, measurable and reversible step in the development of lung cancer and may serve to guide chemopreventative approaches in high-risk smokers.

Accordingly the invention provides a general approach to identifying pathway status (e.g., oncogenic pathway status) in cytologically normal cells of the airway which may be useful as an early predictor of lung disease and/or which may provide targets for therapeutic intervention (e.g., early intervention). According to this approach, oncogenic or other pathways of interest are activated in a cell (e.g., human epithelial cell, human primary epithelial cell culture) in vitro to identify gene expression signatures or patterns which are associated with pathway activation. For example, cells can be perturbed using an adenovirus expressing an activating or necessary component of the pathway of interest (e.g., an adenovirus expressing p110 or other suitable agent). Differentially classified samples (e.g., a sample from a lung cancer patient v. sample from an individual without lung cancer, a sample from a treatment responsive patient v. a sample from a treatment non-responsive patient, etc.) can then be assessed to identify class associations with a gene expression profile indicative of pathway activation. That is, pathway status (e.g.; activation) is correlated with phenotype (e.g., disease state, treatment response, etc.). Thereafter histologically normal airway cells can be tested to identify a gene expression pattern associated with activation of a particular pathway, and based on the correlation between pathway status and phenotype, the phenotype (e.g., disease state such as cancerous, non-cancerous) of the individual from whom the cell sample is obtained can be predicted. In this manner associations between disease state and pathway status (as indicated by gene expression) can be identified, and these associations can be leveraged in therapeutic and prognostic applications. Similarly, the impact of candidate agents and treatment regimens on activation of one or more pathways can be assessed by monitoring gene expression associated with said pathway(s) to identify agents and/or regimens having a desired effect.

The invention also relates to a method of identifying an individual at increased risk of lung disease, comprising determining the activation status of an oncogenic pathway, e.g., the Np63 and/or PI3K pathway, in a cytologically normal airway epithelial cell from said individual. Activation of, e.g., the Np63 and/or PI3K pathway is indicative that said individual is at increased risk of lung disease as compared with an individual in whom the Np63 and/or PI3K pathway is not activated. In particular embodiments the individual is a smoker or a non-smoker. In other embodiments the lung disease is lung cancer, I some embodiments the activation status of multiple pathways (e.g., oncogenic pathways) is assessed simultaneously.

In one embodiment the activation status of the PI3K pathway is determined using gene expression data for one or more (i.e., 1, 2, 3, 4, 5 or more than 5) biomarkers of the PI3K pathway. For example, in some embodiments at least one of said one or more biomarkers is a gene which is increased upon PI3K activation, and in other embodiments at least one of said one or more biomarkers is a gene which is decreased upon PI3K activation. Combinations of biomarkers which are increased and decreased upon PI3K activation may also be used. In particular embodiments at least one of said one or more biomarkers is a gene which is upstream of PI3K activation, while in other embodiments at least one of said one or more biomarkers is a gene which is downstream of PI3K activation.

In one embodiment of the present invention, the isolated nucleic acid is obtained from a cytologically normal airway epithelial cell and used to evaluate expression of a gene or multiple genes using any method known in the art for measuring gene expression, including analysis of mRNA transcripts as well as analysis of DNA methylation.

Methods for assessing mRNA levels are well known to those skilled in the art. In one preferred embodiment, gene expression can be determined by detection of RNA transcripts, for example by Northern blotting, for example, wherein a preparation of RNA is run on a denaturing agarose gel, and transferred to a suitable support, such as activated cellulose, nitrocellulose or glass or nylon membranes. Labeled (e.g. radiolabeled) cDNA or RNA is then hybridized to the preparation, washed and analyzed using methods well known in the art, such as autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994).

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Olin. Chem. 42: 9-13 (1996) and European Patent Application No. 684315; and target mediated amplification, as described by PCT Publication WO 9322461.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

Alternatively, RNA expression, including MRNA expression, can be detected on a DNA array, chip or a microarray. Oligonucleotides corresponding to a gene(s) of interest are immobilized on a chip which is then hybridized with labeled nucleic acids of a test sample obtained from a patient. Positive hybridization signal is obtained with the sample containing transcripts of the gene of interest. Methods of preparing DNA arrays and their use are well known in the art. (See, for example U.S. Pat. Nos. 6,618,679; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

The methods of the present invention can employ solid substrates, including arrays in some preferred embodiments. Methods and techniques applicable to polymer array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098.

Nucleic acid arrays that are useful in the present invention include, but are not limited to those that are commercially available from Affymetrix (Santa Clara, Calif.) under the brand name GeneChip7. Example arrays are shown on the website at affymetrix.com.

The present invention also contemplates many uses for polymers attached to solid substrates. These uses include gene expression monitoring, profiling, library screening, genotyping and diagnostics. Examples of gene expression monitoring, and profiling methods are shown in U.S. Pat. Nos. 5,800,992, 6,013,449, 6,020,135, 6,033,860, 6,040, 138, 6,177,248 and 6,309,822. Examples of genotyping and uses therefore are shown in U.S. Ser. No. 60/319,253, 10/013,598, and U.S. Pat. Nos. 5,856,092, 6,300,063, 5,858, 659, 6,284,460, 6,361,947, 6,368,799 and 6,333,179. Other examples of uses are embodied in U.S. Pat. Nos. 5,871,928, 5,902,723, 6,045,996, 5,541,061, and 6,197,506.

To monitor mRNA levels, for example, mRNA is extracted from the biological sample to be tested, reverse transcribed, and fluorescent-labeled cDNA probes are generated. The microarrays capable of hybridizing to the gene of interest are then probed with the labeled cDNA probes, the slides scanned and fluorescence intensity measured. This intensity correlates with the hybridization intensity and expression levels.

In one preferred embodiment, gene expression is measured using quantitative real time PCR. Quantitative real-time PCR refers to a polymerase chain reaction which is monitored, usually by fluorescence, over time during the amplification process, to measure a parameter related to the extent of amplification of a particular sequence. The amount of fluorescence released during the amplification cycle is proportional to the amount of product amplified in each PCR cycle.

The present invention also contemplates sample preparation methods in certain preferred embodiments. Prior to or concurrent with expression analysis, the nucleic acid sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described, for example, in Dong et al., Genome Research 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described, for example, in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See, for example, U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in provisional U.S. Patent application 60/364,731 and in PCT Application PCT/US99/06097 published as WO99/47964), each of which also is hereby incorporated by reference in its entirety for all purposes.

Examples of methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevansi Bioinformatics: A Practical Guide for Analysis of Gene and Proteins (Wiley & Sons, Inc., 2.sup.nd ed., 2001).

The present invention also makes use of various computer program products and software for a variety of purposes, such as probe design, management of data, analysis, and instrument operation. See, for example, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in, for example, U.S. patent application Ser. No. 10/063,559, 60/349,546, 60/376,003, 60/394,574, 60/403,381.

Throughout this specification, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. In addition, the fractional ranges are also included in the exemplified amounts that are described. Therefore, for example, a range between 1-3 includes fractions such as 1.1, 1.2, 1.3, 1.4, 1.5, 1.6, etc.

In other embodiments the activation status of the PI3K pathway is determined using one or more gene expression products of one or more biomarkers of the PI3K pathway. Said gene expression products may be nucleotide or amino acid products and can be detected using methods known in the art.

In some embodiments of the invention the activation status of the PI3K pathway is determined by assessing the activation of IGF1R, wherein activation of IGF1R is indicative of activation of the PI3K pathway. In other embodiments of the invention the activation status of the PI3K pathway is determined by assessing the activation of PKC, wherein activation of PKC is indicative of activation of the PI3K pathway. In some embodiments of the invention the activation status of the PI3K pathway is determined by assessing the expression of one or more biomarkers for the PI3K pathway disclosed in [29], the teachings of which are incorporated herein by reference.

In one embodiment the activation status of the Np63 pathway is determined using gene expression data for one or more biomarkers of the Np63 pathway. For example, in some embodiments at least one of said one or more biomarkers is a gene which is increased upon Np63 activation, and in other embodiments at least one of said one or more biomarkers is a gene which is decreased upon Np63 activation. Combinations of biomarkers which are increased and decreased upon Np63 activation may also be used. In particular embodiments at least one of said one or more biomarkers is a gene which is upstream of Np63 activation, while in other embodiments at least one of said one or more biomarkers is a gene which is downstream of Np63 activation.

In particular embodiments, expression data for said one or more biomarkers of the Np63 pathway is obtained using an oligonucleotide microarray. In other embodiments the activation status of the Np63 pathway is determined using one or more gene expression products of one or more biomarkers of the Np63 pathway. Said gene expression products may be nucleotide or amino acid products and can be detected using methods known in the art.

The invention also relates to a method of identifying an individual at increased risk of lung disease, comprising determining the activation status of PKC in a cytologically normal airway epithelial cell from said individual, wherein activation of PKC is indicative that said individual is at increased risk of lung disease as compared with an individual in whom PKC is not activated.

The invention further relates to a method of identifying an individual at increased risk of lung disease, comprising determining the activation status of IGF1R in a cytologically normal airway epithelial cell from said individual, wherein activation of IGF1R is indicative that said individual is at increased risk of lung disease as compared with an individual in whom IGF1R is not activated.

In other embodiments the invention provides an oligonucleotide array having immobilized thereon one or more probes for one or more biomarkers of the PI3K pathway, and wherein said array does not have immobilized thereon probes for other biomarkers. In preferred embodiments said one or more biomarkers of the PI3K pathway are selected from the group consisting of IGF1R, PKC, the biomarkers disclosed in [29], and combinations thereof.

The invention also relates to a method of reducing the risk of lung disease in an individual comprising administering to an individual at risk of lung disease one or more agents (e.g., one or more agents, regimens or treatments or combinations thereof) which inhibit the PI3K pathway. In particular embodiments the PI3K pathway is activated in said individual prior to administration of said one or more agents. In one embodiment the lung disease is lung cancer. In another embodiment said one or more agents are administered to said individual prophylactically before the development of lung disease.

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), and Beaucage et al. eds., *Current Protocols in Nucleic Acid Chemistry* John Wiley & Sons, Inc., New York, 2000).

The teachings of all references and websites cited herein are incorporated herein by reference in their entirety. The invention will be further described by the following non-limiting exemplary embodiment.

Exemplary Embodiment

Methods

Patient Population

Airway epithelial brushings were collected from current and former smokers under suspicion of lung cancer who were undergoing diagnostic flexible bronchoscopy from four institutions—Boston University Medical Center, Boston Veterans Administration, Lahey Clinic and St. James's Hospital (previously described in [7], see demographics in Table 1 for samples used in this study). Additional brushes were collected from volunteer healthy current, former and never smokers, as well as smokers with COPD, who were undergoing bronchoscopy (some previously published in [31], demographics in Table 1 and 2). Brushings from the cytologically normal bronchial airway of current and former smokers with airway dysplasia was collected at the University of British Columbia from volunteers who were between 40-74, had pack-years of cumulative smoke history and had one or more sites of bronchial dysplasia on autofluorescence bronchoscopy (see demographics in Table 2). A subset of these volunteers were treated with myo-inositol for a period of 2-3 months, and an additional brush was collected from cytologically-normal airway epithelium at the end of the treatment when autofluorescence bronchoscopy and endobronchial biopsy was used to measure changes in dysplasia (n=20 samples, 10 individuals) [35].

Prospective samples used for biochemical validation were collected at both Boston University Medical Center and University of Utah Hospital. Cytologically-normal bronchial airway brushings were collected on subjects undergoing bronchoscopy for clinical suspicion of lung cancer (see Table 3). Subjects were followed post-bronchoscopy until a final diagnosis or lung cancer or an alternative lung pathology was made.

The study was approved by the Institutional Review Board of all participating institutions and all subjects provided written informed consent.

Sample Collection and Processing

Cytologically normal airway epithelial samples from smokers with and without cancer (n=129, GSE4115), as well as current, former and never smokers (n=104, GSE7895) and smokers with (n=127) and without (n=20) COPD (subset of GSE4115, GSE7895 and GSEYYYY) were collected and hybridized onto Affymetrix HG-U133A microarrays as previously described [7, 31]. For lung tumor and adjacent normal studies, GSE10072 was used [32].

Cytologically normal airway epithelial samples from patients with dysplastic airway lesions at the University of British Columbia were collected before and after 2-3 months of treatment with myo-inositol (n=20, 10 patients with two samples each), as well as six additional samples collected pre-treatment with myo-inositol as part of a dose response study. In that study, bronchial brushing was performed in three separate 6-8th generation bronchial airways using a 1.7 mm diameter bronchial cytology brush (Hobbs Medical, Stafford Springs, Conn.). The brush was retrieved and immediately immersed in RNALater and kept frozen at −80° C. until assayed. Epithelial cell content of representative bronchial brushing samples has been quantitated by cytocentrifugation (ThermoShandon Cytospin, Pittsburgh, Pa.) of the cell pellet and staining with a cytokeratin antibody (Signet, Dedham Mass.). The cells in the bronchial brush contained >90% bronchial epithelial cells. At least 1 μg of each sample were later hybridized to Affymetrix Human Exon ST microarrays according to the manufacturer's protocol. Data from exon arrays were normalized using RMA-sketch in the Affymetrix Expression Console software.

Airway samples collected prospectively for biochemical validation were snap frozen in liquid nitrogen. For a subset of patients, additional brushes were collected and hybridized to Affymetrix HG U133A 2.0 chips. Microarrays were MAS5.0 normalized in Affymetrix Expression Console.

All new expression data for this study is available for download at GEO under the accession GSEYYYY.

Oncogenic Pathway Activation Probability Calculation

Oncogenic pathways from a prior study were utilized, and calculated as detailed previously [13]. Briefly, primary mammary epithelial cells were cultured and allowed to grow to quiescence. Cell cultures were then infected with adenovirus constructs for key members of a specific pathway (e.g., p110, the catalytic subunit of PI3K) in order to activate the pathway of interest. Samples from the perturbed and normal cell culture were processed and hybridized onto Affymetrix microarrays in replicate (approximately 10 samples for each pathway) 18 hours after infection. Before statistical analysis, probesets were filtered based on low expression or low variance (lowest 25% of each was removed). A gene signature for each pathway was defined by selecting 200 probesets based on correlation with the class variable (e.g., perturbed vs. GFP control). Training of the metagene model was accomplished using the perturbed and GFP control samples, by first summarizing the pathway signature in the training data using the most dominant component from singular value decomposition (SVD), and then using Bayesian fitting of a probit regression model. This was done for each of the pathways, and each model was applied to samples of interest. Resulting pathway probabilities were scaled between zero and one. To determine whether an oncogenic pathway was differentially activated, first a rank-sum test was performed, and for p-values less than 0.05, a random permutation analysis was performed. During random permutation, gene identifiers in the dataset of interest (e.g., bronchial airway) were randomized, and a p-value from a Wilcoxon rank sum test was calculated to measure differential activation between class variables (e.g., lung cancer vs. no lung cancer). This was repeated 1,000 times.

Microarray data was initially preprocessed by RMA normalizing, and then corrected for batch effects using DWD [43]. Specifically, to standardize expression data in the development of metagene models, DWD was applied to correct batch effects between the oncogenic pathway signature microarray samples, and bronchial airway microarray samples.

Samples in the prospective series that were run on microarrays in order to compare predicted PI3K activity to biochemical measurements were normalized by mas5 due to the small samples size (n=4). Affymetrix U133A 2.0 chips were used. Pathway activity was calculated using MAS5.0 normalized oncogenic pathway signatures, and no DWD standardization was utilized.

Differences between the metagene model used in this manuscript over the original framework are as follows. Previously, to standardize the training dataset with the samples of interest, singular value decomposition was analyzed across all samples, and the two most dominant components were used in the model. The first component generally explained the variance caused by batch effects between the signature dataset and the dataset of interest, while the second component explained the pathway of interest. To remove the standardization from the model, which also removes influence of the test dataset when training the model, batch correction was done in advance (e.g., using DWD), and SVD was applied to the training and test datasets separately (once for the training set to train the model, and a second time for the dataset of interest to apply the model).

GSEA

Gene Set Enrichment Analysis [30] was calculated using GSEA v2. The genes making up the oncogenic pathway signature for PI3K were used to define a PI3K gene set. Importantly, two gene sets were created, one with genes that are increased upon PI3K activation, and one with genes that are decreased upon PI3K activation. Three different analyses were conducted with GSEA, two of which used microarray data from Affymetrix exon arrays. First, healthy current smokers (n=11) were compared to smokers with dysplasia (n=14). Genes were ranked using the following linear model (as calculated in R):

$$Y = \beta_0 + \beta_1 + \beta_2 + b + \varepsilon$$

Where Y is the expression of a gene, $\beta_0$ is the intercept, $\beta_1$ measures lung cancer risk (whether the sample has dysplasia or not), $\beta_2$ is the cumulative cigarette smoke exposure for each person (pack-years), b is a random effect correcting for batch differences, and $\varepsilon$ is the error term. The coefficient of $\beta_1$ was used to rank the genes for GSEA. Second, to compare pre- and post-treatment with myo-inositol, samples were ranked using a paired Wilcoxon rank sum test. The GSEA analysis done in the U133A airway dataset used the default signal to noise ranking. 100 gene set permutations were used to calculate FDR.

Kinase Assay

80% confluent BEAS-2B, BT549, or HEK293 cells were starved in BEBM, RPMI, or DMEM medium, respectively (Clonetics, GibcoBRL). This media contained either 0.1% added supplements for the BEAS-2B cells or 0.1% fetal bovine serum for BT549 and HEK293 cells for 24 hrs. Cells were then pretreated with increased concentrations of myo-inositol (Sigma), or LY294002 (Sigma) for 16 hrs. at 37° C. Prior stimulation, the cells were treated with fresh drugs for another 30 min, then 500 uM of insulin (SIGMA) were added for 15 minutes at 37° C. The cells were lysed in RIPA buffer (20 mM TRIS (pH 7.4), 150 mM NaCl, 1% NP-40, 0.5% Sodium Deoxycholate, 1 mM EDTA, 0.1% SDS) containing 0.1 mM sodium orthovanadate, 2 mM PMSF, 100 uM protease inhibitors (Sigma). Lysates were centrifuged at 14000 rpm for 20 minutes at 4° C. and incubated with monoclonal anti-p85 PI3K (Santa Cruz) antibody for 1 hr at 4° C. The bounded proteins were precipitated with 50 ul of 50% slurry protein G Sepharose (Sigma) and washed three times with lysis buffer, three times with buffer containing 0.1 mM Tris (pH 7.4), 5 mM LiCl, 0.1 mM sodium orthovanadate, and two times with buffer containing 10 mM Tris (pH 7.4), 150 mM NaCl, 5 mM EDTA, 0.1 mM sodium orthovanadate. The beads were washed in kinase buffer (50 mM Tris (pH 7.4), 10 mM $MgCl_2$) containing 20 uM cold ATP (Sigma), and resuspended in 45 ul of kinase buffer containing 5 ul of L-a-phosphatidylinositol-4,5-bisphosphate (Avanti Polar Lipids) (1 mg/ml), and 20 uCi ATP (32-P) for 20 minutes at RT. The reactions were stopped by addition of 100 ul 1N HCl, and the lipids were extracted with 160 ul of CHCl3/MeOH (1:1). The phosphorylated products were separated by TLC on Silica 60 plates pretreated with potassium oxalate in a CHCl3/MeOH/NH4 solution (45:35:1.5). The production of PIP3 was evaluated by autoradiography and quantified by densitometry analysis and scintillation analysis. All experiments for each cell line were repeated at least twice with similar results.

Western Blot Analysis

Patient tissue samples were collected by bronchoscopy and snap frozen immediately in liquid nitrogen. Cell extracts from bronchoscopy brushes were prepared by adding 200 ul of RIPA buffer. To facilitate the detachment of the cells from the brushes, the tubes were vortexed three times for 5 seconds. Both cell and bronchoscopy brushing extracts were centrifuged at 14000 rpm for 20 minutes at 4° C. and the pellets discarded. The protein yield was quantified by Bradford assay, and equivalent amount of protein was loaded to 7% SDS-PAGE gels. The membrane were blocked for 1 h in blocking buffer (Tris buffer saline containing 0.1% Tween 20 and 2.5% BSA, or Tris buffer saline containing 0.1% of Tween 20 and 5% low fat milk), and placed in primary antibody (Tris buffer saline containing 0.1% Tween 20 and 2.5% BSA, 0.02% sodium azide) overnight at 4° C. The primary antibodies used in this study are the followed: rabbit phospho-PKC (pan) (βII Ser660) ratio 1:100 (Cell Signaling Techn.); rabbit phospho-IGF-I Receptor β (Tyr1131)/Insulin Receptor β (Tyr 1146) ratio 1:100 (Cell Signaling Techn.); rabbit phospho-PLCγ1 (Tyr783), ratio 1:500 (Cell Signaling Techn.); rabbit phospho-AKT (Ser473) ratio 1:100 (Cell Signaling Techn.); goat PI3-Kinase p110α (C17) ratio 1:50 (Santa Cruz), rabbit phospho-ERK ratio 1:100 (Cell Signaling) rabbit GAPDH, ratio 1:1000 (AbCam). Nitrocellulose were washed three times in Tris buffer saline containing 0.1% Tween 20 and/or 0.1% NP-40. Primary antibody was detected using horseradish peroxidase-linked secondary antibody and visualized with the ECL Plus Western Blot Detection system (GE Healthcare).

Results

PI3K Pathway Activation in Cytologically Normal Bronchial Airway Epithelial Cells of Smokers with Lung Cancer Cytologically normal bronchial airway epithelial cell brushings were obtained from current and former smokers undergoing flexible bronchoscopy for suspicion of lung cancer and were hybridized to DNA microarrays as previously described [7] (n=129, see patient demographics in Table 1). To help elucidate oncogenic pathway signaling changes in these cells, we utilized a previously published gene expression dataset and computational approach [13, 26-28]. Oncogenic pathway signatures [13] were experimentally derived by activating a pathway via expression of a specific oncogene in primary human epithelial cells. A gene expression signature was then defined by identifying which genes are altered following pathway activation, and used to predict pathway activity in other in vivo samples. Using this methodology, oncogenic pathway activation probabilities for seven signaling pathways (Ras, Myc, E2F3, Src, β-catenin, ΔNp63 and phosphatidylinositol 3' kinase (PI3K)) were calculated for the bronchial airway epithelial of current and former smokers with suspicion for lung cancer [7]. It is important to note that although approximately half of these patients were ultimately diagnosed with primary lung cancer (the remainder were found to have alternate lung pathologies), the brushings collected from the proximal mainstem bronchus (i.e. not adjacent to the tumor or lung lesion), were cytologically normal and were >90% epithelial. Thus, a priori one would not expect differential oncogenic pathway activity in the normal airway of smokers with lung cancer.

Of the seven pathways tested, only two were found to be significantly and differentially activated in the airway of smokers with lung cancer compared to controls with alternate lung pathologies after a random permutation analysis: ΔNp63 and PI3K (p<0.001, FIG. 1A). Furthermore, the genes that have been found to play roles in the phosphatidylinositol signaling system pathway [29, the teachings of which are incorporated by reference herein] were also found to be significantly upregulated in lung cancer patients using Gene Set Enrichment Analysis [30] (GSEA, p=0.034, FDR q=0.099). Upregulation of PI3K was not limited to a specific cancer cell type, tumor location or tumor stage (data not shown).

PI3K Activation is not Significantly Correlated to Cumulative Smoke Exposure or COPD We next sought to determine whether the increased pathway activity of PI3K was due to the presence of cancer in the lung, or caused by other confounding factors such as differences in cumulative smoke exposure (patients with cancer had higher cumulative exposure, see Table 1) or other pulmonary diseases. First, an ANCOVA using cumulative smoke exposure as a covariate was used to test for differential pathway activation between patients with and without lung cancer. PI3K (p=2.08×10-8) remained significantly differentially activated after addressing the possible confounding influence of differences in tobacco exposure. Second, using a whole-genome gene expression dataset of bronchial airway epithelium collected from current (n=52), former (n=31) and never (n=21) healthy smokers [31], we calculated the pathway activation probabilities for all seven pathways using the same methodologies previously described. While none of the seven pathways were differentially activated between healthy current, never and former smokers, the ΔNp63 pathway trended towards being significantly activated when comparing never and current smokers (p=0.09, FIG. 1B). Finally, using a bronchial airway gene expression dataset obtained from smokers with (n=17) and without (n=20) chronic obstructive pulmonary disease (COPD), Ras was the only pathway that was differentially activated (p<0.001, data not shown) (FIG. 1C). This lends evidence that the significant differential) activation of the oncogenic pathway PI3K in the normal bronchial airway is specific to individuals with lung cancer, though the mechanism of differential activation is unknown. Due to the known deregulation of p53 related pathways (such as ΔNp63) in response to environmental stressors, as well as the lack of any known therapeutic modulators of the p53/p63 pathway, we chose to focus on the PI3K pathway for all further studies.

PI3K is Activated in Lung Cancer Tissue

Figure 2:
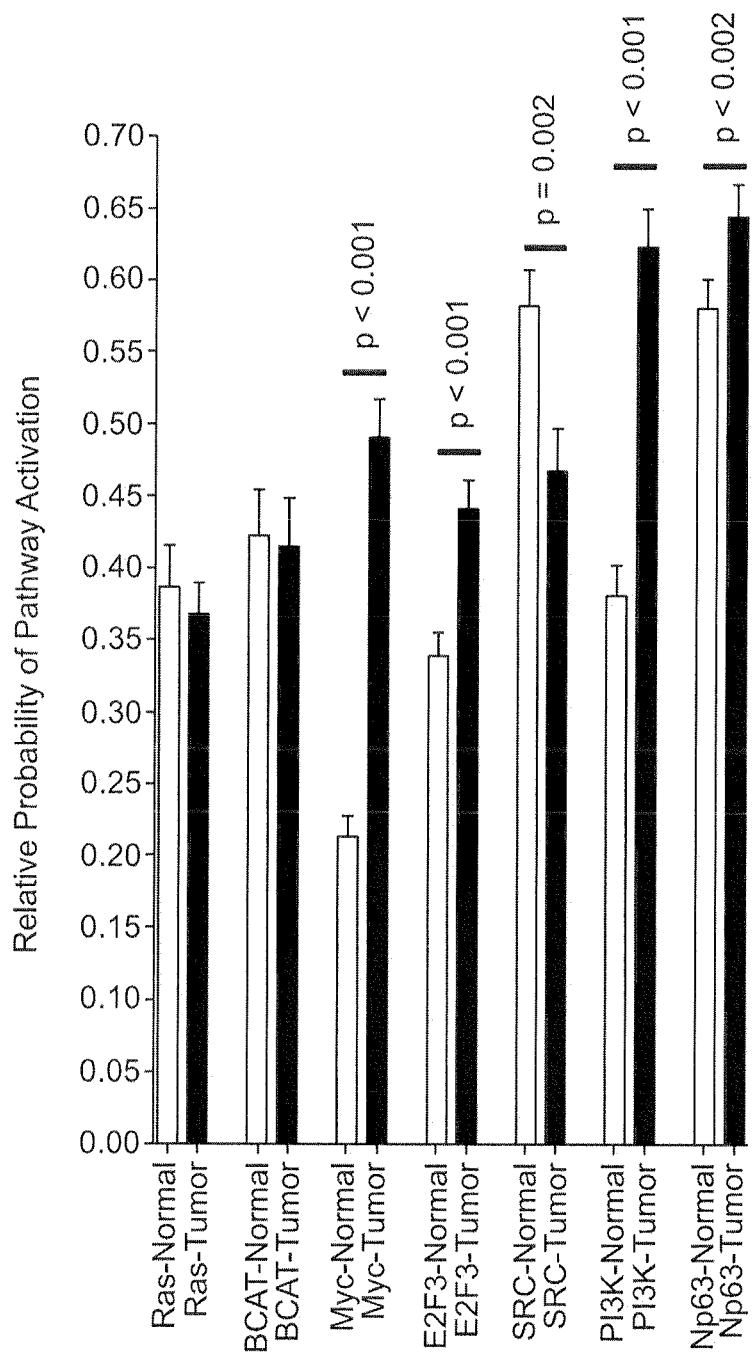
FIG. 2 shows oncogenic pathway activity in lung tumor and adjacent normal tissue. Oncogenic pathway activity was calculated for a dataset of lung adenocarcinoma and adjacent normal tissue [32]. An increase in PI3K (p<0.001) and ΔNp63 (p=0.002) was observed when comparing adjacent normal and its paired tumor sample. Increases were also seen in Myc and E2F3, and there was a decrease in Src. Error whiskers are reported as SEM.

The deregulation of PI3K in cytologically normal airway epithelial cells of patients with lung cancer led us to examine PI3K activity in lung cancer tissue. We would expect a significant increase in oncogenic pathways essential for tumor growth and survival during lung cancer development. For this analysis, we used a published dataset comprised of lung adenocarcinoma and matched adjacent non-tumor tissue (n=107) [32]. Pathway status was predicted using the same genomic approach detailed above. As shown in FIG. 2, malignant lung tumors had a highly significant (p<0.001) increase in PI3K activity as compared to the adjacent non-tumor tissue. ΔNp63 pathway was also increased to a lesser extent in tumor cells (p=0.002). This result highlights a central role for the PI3K pathway in the malignant progression of cells, and supports our hypothesis that PI3K activation is important for lung cancer tumorigenesis. A significant increase was also seen for the Myc, E2F3 and Src pathways in lung tumors, confirming their roles in lung tumor growth and development. As lung tumors are comprised of dividing cells and have higher levels of proliferation than normal tissue, we would expect pathway involved in cell growth (Myc, E2F3, Src) to also be increased in this analysis.

Biochemical Analysis of PI3K Pathway Activity in the Bronchial Airway

To validate our gene expression findings, we measured PI3K enzymatic activity in a prospectively collected cohort of cytologically-normal airway epithelial samples from subjects undergoing bronchoscopy for clinical suspicion of lung cancer. Samples were independently obtained from Boston University Medical Center and University of Utah Hospital between October 2007 and June 2008. Subjects were followed post-bronchoscopy until a final diagnosis of lung cancer or an alternate lung pathology was made. Importantly, subjects without lung cancer had a range of other pathologies, including metastatic cancer of non-lung origin, sarcoidosis, septic emboli, and pneumonia. Following protein extraction from the airway brushings, a PI3K kinase assay was performed. Based on our genomic predictions, we would expect a majority of samples from patients with cancer to have high PI3K activity and only a minority of the samples from patients with alternative pathologies to have high PI3K activity.

As seen in FIG. 3A, PI3K showed increased activation in the majority of patients with lung cancer (70% of the lung cancer samples in the genomic analysis were in the top half of PI3K activity), as compared to patients without lung cancer (30%). Specifically, we see high correlation between PI3K activity and lung cancer status for both cohorts (Boston: R=0.499, Utah: R=0.389). For a subset of these samples (n=4), we were able to collect additional bronchial epithelial cells to perform microarray analysis and predict PI3K activity using the same approach as was used on the original dataset. Predicted PI3K activity was correlated with the PI3K levels measured biochemically within the same individual (R=0.48). Together, these results support the conclusion that PI3K activity is increased in the normal airway of patients with lung cancer and validate our computational predictions of PI3K activity calculated from gene expression data. These results are even more striking when considering the variety of pathologies in the control patients that might also affect PI3K activity.

In an attempt to further define the causes and consequences of elevated PI3K activity, we performed Western Blotting analysis of the phosphorylation state of key PI3K pathway components. Phosphorylation of IGF1R (Boston: R=0.91, Utah: R=0.34), but not HER2 (Boston R=−0.61, Utah R=−0.41), positively correlated to PI3K kinase activity (FIG. 3B), suggestive of this receptor being an upstream effector for PI3K activation in the normal airway epithelial tissue of patients with lung cancer. Correlation between biochemically measured PI3K activity and IGF1R in patients with lung cancer shows a high positive correlation, further supporting a potential relationship between IGF1R activation and PI3K activity (Boston R=0.98, Utah R. 0.90) (FIG. 3B). Next, measured phosphorylation of Akt and PKC, the major downstream effectors of PI3K, was measured. PKC had higher correlation with biochemically measured PI3K activity in patients with lung cancer, while no significant correlation was seen for Akt (FIG. 3B), again highlighting activation of specific PI3K pathways in patients with lung cancer. Cumulatively, these results support our genomic findings that PI3K activity is enriched in the normal lung cells of patients with lung cancer compared to patients with other pathologies, and the activation of IGF1R is a potential mechanism for this activity [33, 34].

PI3K Pathway Activation in High-Risk Smokers with Dysplasia

Figure 4:
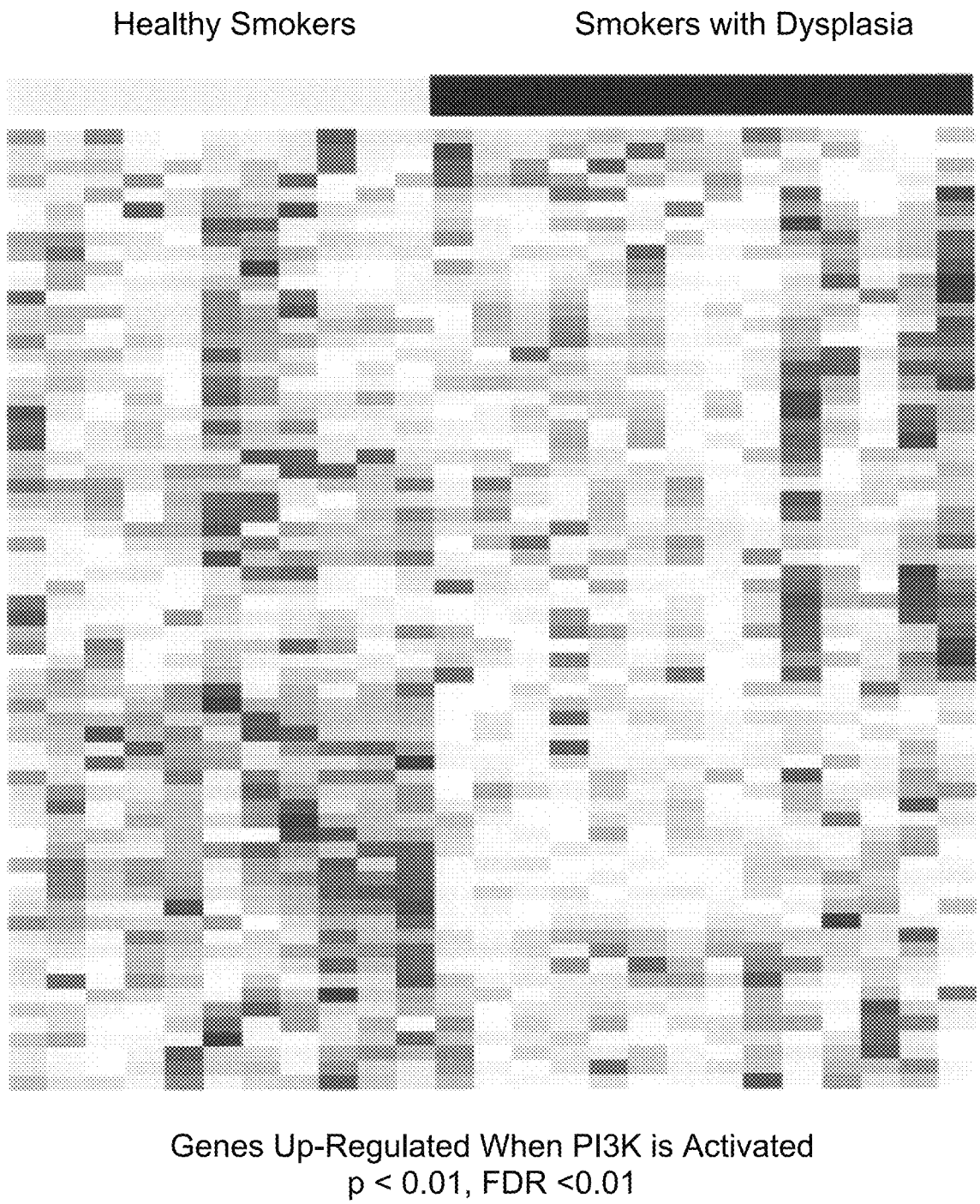
FIG. 4 demonstrates that smokers with dysplasia have an increased activation of the PI3K pathway. Genes that increase when the PI3K pathway is activated, as defined by in vitro perturbation, are displayed in a heatmap. Blue represents low expression of a gene, while red represents higher expression of a gene. When comparing the expression levels of these genes in the cytologically normal bronchial airway of smokers with dysplasia against healthy smokers, an increased activation of the PI3K pathway in smokers with dysplasia was observed. GSEA was used to quantify the enrichment of this gene set (p<0.001, FDR Q<0.001). Genes were ranked for GSEA using a linear model that takes into account dysplasia status, pack-years as well as a random variable accounting for batch effects.

To evaluate the hypothesis that an increased activation of PI3K is an early event in the development of lung cancer, we compared gene expression in cytologically normal airway epithelia from a group of healthy smokers (n=11) to a group of smokers with moderate-severe airway dysplasia (n=14, from [35]) (See Table 2). As dysplasia is considered to be a pre-neoplastic event, this cohort represents "high-risk" smokers who have an increased likelihood of getting lung cancer [36, 37]. If high-risk smokers with dysplasia have higher levels of PI3K than healthy smokers, it would suggest that the increased activity in the airway epithelium precede the development of lung cancer. The high-risk cohort, as well as a cohort of healthy current smokers, was hybridized to Affymetrix Human Exon arrays. Due to platform differences with the oncogenic pathway signatures, we were unable to use the metagene model to calculate pathway activity. Instead, GSEA was used to compare PI3K activity between the two groups, and the PI3K gene signature defined by the in vitro experiments was split into two gene sets defined by the genes that go up or down with PI3K activation (PI3K_Up, PI3K_Down). Given that there were significant differences in cumulative tobacco exposure between the two groups, a linear model incorporating both batch effects and pack-years was used to rank the genes for use in GSEA. A significant increase in PI3K activity in the cytologically normal airway of subjects with dysplasia was found (p<0.001, FDR Q=0.022 and p<0.001, Q<0.001 for PI3K_Up and PI3K_Down gene sets respectively) (FIG. 4). The increased activity of PI3K in the airway of people with dysplasia indicates that the deregulation of PI3K is an early event in lung cancer tumorigenesis.

Reversibility of PI3K Activity in High-Risk Smokers Treated with Myo-Inositol

Given elevated PI3K activity in both high-risk smokers as well as smokers with lung cancer, we next wanted to determine if a decrease of PI3K activity would correlate with regression of dysplastic lesions. A recent phase 1 clinical study published by Lam et al. [35] studied myo-inositol as a lung cancer chemoprophylactic agent in high-risk smokers. In this study, volunteer smokers with ≥30 pack-years of smoking history were screened for the presence of dysplasia in their airway using autofluorescent bronchoscopy. Ten current and former smokers with moderate-severe dysplasia documented on endobronchial biopsy were then given oral myo-inositol for 2-3 months, and the status of their dysplastic lesions was again measured by repeat endobronchial biopsy of the site. When compared to control patients who were treated with placebo, myo-inositol was found to significantly increase the rate of dysplastic regression. Airway brushings of cytologically normal bronchial epithelium were also collected both before and after treatment, and gene expression profiling was performed (see demographics in Table 2).

GSEA analysis was again used to measure changes in the expression of genes in the PI3K pathway. When comparing before treatment with myo-inositol versus after treatment, subjects who did respond to treatment (n=6, 12 samples) showed increased expression of genes in the PI3K Down gene set (p=0.04, FDR Q=0.177), which is suggestive of a decrease in PI3K levels following treatment with myo-inositol. Those that did not respond to treatment (n=3, 6 samples) had no change in the levels of the PI3K gene sets. The decrease in airway PI3K activity seen in patients who respond to myo-inositol demonstrates that regression of dysplasia is correlated to the activity level of this pathway.

Myo-Inositol as a PI3K Inhibitor

A reduction in PI3K activity in patients that responded to myo-inositol with a regression of dysplasia in their airway reinforces the association between elevated PI3K activity levels and the presence of pre-neoplastic airway lesions. However, the mechanism of action of myo-inositol has remained undefined, and the study was limited by a relatively small sample size. To further explore the relationship between myo-inositol and the PI3K activity, we tested the ability of myo-inositol to inhibit PI3K in vitro. Following activation of PI3K by treating cells with insulin, cells were treated with increasing doses of either myo-inositol or LY-294002 (a known PI3K inhibitor). PI3K activity, as measured by PIP3 levels, was then quantified using a standard kinase assay protocol [38, 39]. For this experiment, three different cell lines were analyzed in replicate: BEAS-2B (airway), BT549 (breast cancer) and HEK293 (embryonic kidney). In all three cell lines, myo-inositol inhibited PI3K activity levels in a dose-dependent manner (FIG. 5). Thus, myo-inositol is an inhibitor of PI3K, and has chemoprophylactic properties associated with regression of dysplasia in airway epithelial cells.

Tables:

TABLE 1

Patient demographics for the Affymetrix U133A platform datasets used in this study. These cohorts were used to explore differences in oncogenic activity in the cytologically normal airway epithelium of smokers with lung cancer. Average number for clinical variables is shown, with the standard deviation in parenthesis. Under "Smoking Status," C = current smoker, and F = Former smoker. COPD = Chronic Obstructive Pulmonary Disease. All datasets consist of samples collected via brushing of cytologically-normal bronchial airway epithelium obtained during bronchoscopy.

| | Primary Dataset | | Never/Former/Current Smoker Dataset | | | COPD Dataset | |
|---|---|---|---|---|---|---|---|
| | Lung Cancer | No Lung Cancer | New | Former | Current | No COPD | COPD |
| Samples | 60 | 69 | 21 | 31 | 52 | 20 | 17 |
| Age | 64.1 (9)* | 49.8 (15.2)* | 32.3 (10.7)* | 55.9 (14.7)* | 48.6 (15.2)* | 43.6 (9.3)* | 60.4 (12.3)* |
| Pyers | 57.4 (25.6)* | 29.4 (27.3)* | | 34.0 (30.1) | 34.5 (34.2) | 33.5 (25.9)* | 57.4 (27.9)* |
| Smoking Status | 51.7% F, 48.3% C | 37.3% F, 62.3% C | | 100% F | 100% C | 100% C | 100% C |
| Months Since Quit (Formers) | 113 (118) | 158 (159) | | 145.2 (162.8) | | | |

*Feature is significantly different between the classes of that dataset (p < 0.05)

TABLE 2

Patient demographics for the Affymetrix exon array platform datasets used in this study. These cohorts were used to explore PI3K activity prior to the development of lung cancer, as well as changes in PI3K activity following treatment with a lung cancer chemoprophylaxis agent (myo-inositol). Average number for clinical variables is shown, with the standard deviation in parenthesis. Under "Smoking Status," C = current smoker, and F = former smoker. All datasets consist of samples collected via brushing of cytologically-normal bronchial airway epithelium obtained during bronchoscopy.

| | Smokers With Dysplasia (Myo-inositol dataset) | | Healthy |
|---|---|---|---|
| | Matched Samples Before and After Treatment | Airway with Dysplasia | Smokers Current |
| Samples | 20 (10 before, 10 after) | 6 | 11 |
| Age | 61.7 (8.3) | 64.5 (7.1) | 36.5 (10.0) |
| Pack-Years | 42.9 (23.7) | 59.8 (17.7) | 12.4 (92) |
| Smoking Status | 70% F, 30% C | 100% C | 100% C |
| Months Since Quit (Formers) | 145.7 (89.9) | | |

* Age, Pack-years significantly different between dysplasia and healthy smoker datasets (p < 0.05)

REFERENCES

1. United States. Public Health Service. Office of the Surgeon General, National Center for Chronic Disease Prevention and Health Promotion (U.S.). Office on Smoking and Health., and Centers for Disease Control and Prevention (U.S.), The health consequences of smoking: a report of the Surgeon General: executive summary. 2004, [Atlanta, Ga.]: U.S. Dept. of Health and Human Services Pubic Health Service Office of the Surgeon General.
2. Powell, C. A., et al., Loss of heterozygosity in epithelial cells obtained by bronchial brushing: clinical utility in lung cancer. Clin Cancer Res, 1999. 5(8): p. 2025-34.

3. Wistuba, I I, et al., Molecular damage in the bronchial epithelium of current and former smokers. J Natl Cancer Inst, 1997. 89(18): p. 1366-73.
4. Guo, M., et al., Promoter hypermethylation of resected bronchial margins: a field defect of changes? Clin Cancer Res, 2004. 10(15): p. 5131-6.
5. Franklin, W. A., et al., Widely dispersed p53 mutation in respiratory epithelium. A novel mechanism for field carcinogenesis. J Clin Invest, 1997. 100(8): p. 2133-7.
6. Miyazu, Y. M., et al., Telomerase expression in noncancerous bronchial epithelia is a possible marker of early development of lung cancer. Cancer Res, 2005. 65(21): p. 9623-7.
7. Spira, A., et al., Airway epithelial gene expression in the diagnostic evaluation of smokers with suspect lung cancer. Nat Med, 2007. 13(3): p. 361-6.
8. Beane, J., et al., A Prediction Model for Lung Cancer Diagnosis that Integrates Genomic and Clinical Features 10.1158/1940-6207.CAPR-08-0011. Cancer Prev Res, 2008. 1(1): p. 56-64.
9. Marinov, M., B. Fischer, and A. Arcaro, Targeting mTOR signaling in lung cancer. Crit Rev Oncol Hematol, 2007. 63(2): p. 172-82.
10. Takahashi, T., et al., p53: a frequent target for genetic abnormalities in lung cancer. Science, 1989, 246(4929): p. 491-4.
11. Downward, J., Targeting RAS signalling pathways in cancer therapy. Nat Rev Cancer, 2003. 3(1): p. 11-22.
12. Grepmeier, U., et al., Deletions at chromosome 2q and 12p are early and frequent molecular alterations in bronchial epithelium and NSCLC of long-term smokers. Int J Oncol, 2005, 27(2): p. 481-8.
13. Bild, A. H., et al., Oncogenic pathway signatures in human cancers as a guide to targeted therapies. Nature, 2006. 439(7074): p. 353-7.
14. Massague, J., Sorting out breast-cancer gene signatures. N Engl J Med, 2007. 356(3): p. 294-7.
15. Huang, F., et al., Identification of candidate molecular markers predicting sensitivity in solid tumors to dasatinib: rationale for patient selection. Cancer Res, 2007. 67(5): p. 2226-38.
16. Sato, M., et al., A translational view of the molecular pathogenesis of lung cancer. J Thorac Oncol, 2007. 2(4): p. 327-43.
17. Rhodes, D. R., et al., Molecular concepts analysis links tumors, pathways, mechanisms, and drugs. Neoplasia, 2007.
18. Finn, R. S., et al., Dasatinib, an orally active small molecule inhibitor of both the src and abl kinases, selectively inhibits growth of basal-type/"triple-negative" breast cancer cell lines growing in vitro. Breast Cancer Res Treat, 2007. 105(3): p. 319-26.
19. Horvath, S., et al., Analysis of oncogenic signaling networks in glioblastoma identifies ASPM as a molecular target. Proc Natl Acad Sci USA, 2006. 103(46): p. 17402-7.
20. Garraway, L. A., et al., Integrative genomic analyses identify MITF as a lineage survival oncogene amplified in malignant melanoma. Nature, 2005. 436(7047): p. 117-22.
21. Lamb, J., et al., The Connectivity Map: using gene-expression signatures to connect small molecules, genes, and disease. Science, 2006. 313(5795): p. 1929-35,
22. Baselga, J., Targeting tyrosine kinases in cancer: the second wave. Science, 2006. 312(5777): p. 1175-8.
23. Paez, J. G., et al., EGFR mutations in lung cancer: correlation with clinical response to gefitinib therapy. Science, 2004. 304(5676): p. 1497-500.
24. van't Veer, L. J. and R. Bernards, Enabling personalized cancer medicine through analysis of gene-expression patterns. Nature, 2008. 452(7187): p. 564-70.
25. Hennessy, B. T., et al., Exploiting the PI3K/AKT pathway for cancer drug discovery. Nat Rev Drug Discov, 2005. 4(12): p. 988-1004.
26. Black, E. P., et al., Distinctions in the specificity of E2F function revealed by gene expression signatures. Proc Natl Acad Sci USA, 2005. 102(44): p. 15948-53.
27. Black, E. P., et al., Distinct gene expression phenotypes of cells lacking Rb and Rb family members. Cancer Res, 2003. 63(13): p. 3716-23.
28. Huang, E., et al., Gene expression phenotypic models that predict the activity of oncogenic pathways. Nat Genet, 2003. 34(2): p. 226-30.
29. Kanehisa, M., et al., KEGG for linking genomes to life and the environment. Nucleic Acids Res, 2008. 36(Database issue): p. D480-4.
30. Subramanian, A., et al., Gene set enrichment analysis: a knowledge-based approach for interpreting genome-wide expression profiles. Proc Natl Acad Sci USA, 2005. 102(43): p. 15545-50.
31. Beane, J., et al., Reversible and permanent effects of tobacco smoke exposure on airway epithelial gene expression. Genome Biol, 2007. 8(9): p. R201.
32. Landi, M. T., et al., Gene expression signature of cigarette smoking and its role in lung adenocarcinoma development and survival. PLoS ONE, 2008. 3(2): p. e1651.
33. Mackay, H. J. and C. J. Twelves, Targeting the protein kinase C family: are we there yet? Nat Rev Cancer, 2007. 7(7): p. 554-62.
34. Dempsey, E. C., C. D. Cool, and C. M. Littler, Lung disease and PKCs. Pharmacol Res, 2007. 55(6): p. 545-59.
35. Lam, S., et al., A phase I study of myo-inositol for lung cancer chemoprevention. Cancer Epidemiol Biomarkers Prev, 2006. 15(8); p. 1526-31.
36. Greenberg, A. K., H. Yee, and W. N. Rom, Preneoplastic lesions of the lung. Respir Res, 2002. 3: p. 20.
37. Salaun, M., et al., Molecular predictive factors for progression of high-grade preinvasive bronchial lesions. Am J Respir Crit Care Med, 2008. 177(8): p. 880-6.
38. Kamalati, T., et al., Expression of the BRK tyrosine kinase in mammary epithelial cells enhances the coupling of EGF signalling to PI 3-kinase and Akt, via erbB3 phosphorylation. Oncogene, 2000. 19(48): p. 5471-6.
39. Whitman, M., et al., Association of phosphatidylinositol kinase activity with polyoma middle-T competent for transformation. Nature, 1985. 315(6016): p. 239-42.
40. Yang, Y., et al., Phosphatidylinositol 3-kinase mediates bronchioalveolar stem cell expansion in mouse models of oncogenic K-ras-induced lung cancer. PLoS ONE, 2008. 3(5): p. e2220.
41. Bader, A. G., et al., Oncogenic PI3K deregulates transcription and translation. Nat Rev Cancer, 2005. 5(12): p. 921-9.
42. Yamamoto, H., et al., PIK3CA mutations and copy number gains in human lung cancers. Cancer Res, 2008. 68(17): p. 6913-21.
43. Benito, M., et al., Adjustment of systematic microarray data biases. Bioinformatics, 2004. 20(1): p. 105-14.

We claim:

1. A method of processing a sample, comprising obtaining an airway epithelial sample by airway epithelial brushing comprising a cytologically normal airway epithelial cell and measuring the phosphorylation of IGF1R with an antibody in the cytologically normal airway epithelial cell.

2. The method of claim 1, wherein the sample is obtained from a smoker or former smoker.

3. The method of claim 2, wherein the smoker or former smoker is suspected of having lung cancer.

* * * * *